(12) United States Patent
Behfar et al.

(10) Patent No.: US 12,036,232 B2
(45) Date of Patent: Jul. 16, 2024

(54) PARTICLE-MEDIATED DELIVERY OF BIOLOGICS

(71) Applicant: MAYO FOUNDATION FOR MEDICAL EDUCATION AND RESEARCH, Rochester, MN (US)

(72) Inventors: Atta Behfar, Rochester, MN (US); Andre Terzic, Rochester, MN (US)

(73) Assignee: MAYO FOUNDATION FOR MEDICAL EDUCATION AND RESEARCH, Rochester, MN (US)

( * ) Notice: Subject to any disclaimer, the term of this patent is extended or adjusted under 35 U.S.C. 154(b) by 0 days.

(21) Appl. No.: 17/567,482

(22) Filed: Jan. 3, 2022

(65) Prior Publication Data

US 2022/0152084 A1    May 19, 2022

Related U.S. Application Data

(63) Continuation of application No. 16/463,053, filed as application No. PCT/US2017/063060 on Nov. 22, 2017, now abandoned.

(60) Provisional application No. 62/426,090, filed on Nov. 23, 2016.

(51) Int. Cl.

| | |
|---|---|
| *C07H 21/02* | (2006.01) |
| *A61K 9/00* | (2006.01) |
| *A61K 9/06* | (2006.01) |
| *A61K 9/127* | (2006.01) |
| *A61K 9/48* | (2006.01) |
| *A61K 9/51* | (2006.01) |
| *A61K 31/7105* | (2006.01) |
| *A61K 47/36* | (2006.01) |
| *A61K 48/00* | (2006.01) |
| *C07H 21/04* | (2006.01) |
| *C12N 15/113* | (2010.01) |

(52) U.S. Cl.
CPC ........ *A61K 31/7105* (2013.01); *A61K 9/0019* (2013.01); *A61K 9/06* (2013.01); *A61K 9/127* (2013.01); *A61K 9/48* (2013.01); *A61K 9/5161* (2013.01); *A61K 47/36* (2013.01); *A61K 48/00* (2013.01); *C07H 21/04* (2013.01); *C12N 15/113* (2013.01)

(58) Field of Classification Search
CPC .......................... C12N 15/113; C12N 2310/14
See application file for complete search history.

(56) References Cited

U.S. PATENT DOCUMENTS

| | | |
|---|---|---|
| 2011/0008451 A1 | 1/2011 | Saltzman et al. |
| 2013/0259923 A1 | 10/2013 | Bancel et al. |
| 2015/0110859 A1 | 4/2015 | Heartlein et al. |
| 2015/0366997 A1 | 12/2015 | Guild |
| 2016/0024171 A1 | 1/2016 | Schrum et al. |
| 2016/0152987 A1 | 6/2016 | Saltzman et al. |
| 2016/0206697 A1 | 7/2016 | Behfar et al. |

FOREIGN PATENT DOCUMENTS

| | | |
|---|---|---|
| JP | 2000-504716 A5 | 11/2004 |
| JP | 2009-527768 A | 7/2009 |
| JP | 2014-509617 A | 4/2014 |
| JP | 2014-523411 A | 9/2014 |
| JP | 2015-501844 A | 1/2015 |
| JP | 2015-535430 A | 12/2015 |
| JP | 2016-534992 A | 11/2016 |
| WO | WO 99/14346 A2 | 3/1999 |
| WO | WO 2007/050643 A2 | 5/2007 |
| WO | WO 2008/093195 A2 | 8/2008 |
| WO | WO 2011/068810 A1 | 6/2011 |
| WO | WO 2012/138453 A1 | 10/2012 |
| WO | WO 2015/034897 A1 | 3/2015 |
| WO | WO 2015/061467 A1 | 4/2015 |
| WO | WO 2015/148247 A1 | 10/2015 |
| WO | WO 2016/075154 A1 | 5/2016 |
| WO | WO 2019/226875 A1 | 11/2019 |

OTHER PUBLICATIONS

Yang et al. (Lab Chip, 2012, 12, 2097-2102).*
Tran et al. (Expert Opinion on Drug Delivery, 2014, 11:7, 1061-1074).*
Kaewsaneha et al. (ACS Appl. Mater. Interfaces 2013, 5, 6, 1857-1869).*
Liu et al. (Journal of Colloid and Interface Science, 466, 2016, 20-27).*
Wan et al. (Polymers, 2012, 4, 1084-1108).*
Ogun et al., "Biochemistry, Transferrin", *StatPearls—NCBI Bookshelf*, Nov. 16, 2022, 4 pages.
Komei et al., "Follistatin-Like 1 Regulates Hypertrophy in Heart Failure With Preserved Ejection Fraction", *Pre-Clinical Research*, Jan. 1, 2016, 15 pages.
European Patent Application No. 21205388.8, filed Oct. 28, 2021; Office Action issued Mar. 15, 2023, 10 pages.
Extended European Search Report for European Application No. 21205388.8 dated May 12, 2022, 35 pages.
Boucek et al., "Ex vivo paracrine properties of cardiac tissue: Effects of chronic heart failure", *Journal of Controlled Release*, 150, 2011, 238-247.
De Temmerman et al., "mRNA-Lipoplex loaded microbubble contrast agents for ultrasound-assisted transfection of dendritic cells", *Biomaterials*, 32, 2011, 9128-9135.
Devoldere et al., "Evading innate immunity in nonviral mRNA delivery: don't shoot the messenger", *Drug Discovery Today*, 21, 1, Jan. 2016, 11-25.

(Continued)

*Primary Examiner* — Amy Rose Hudson
(74) *Attorney, Agent, or Firm* — Mueting Raasch Group

(57) ABSTRACT

A composition for delivering a biologic to a subject generally includes a particulate substrate and an mRNA encapsulated by the particulate substrate. In some cases, the mRNA may be indirectly attached to the particulate substrate. The mRNA encodes at least one therapeutic polypeptide. The composition may be delivered to a tissue of a subject to provide a therapeutic benefit to the tissue.

15 Claims, 26 Drawing Sheets

Specification includes a Sequence Listing.

(56) References Cited

OTHER PUBLICATIONS

European Search Report (extended) for EP App. No. 17873643.5 dated Sep. 4, 2020, 26 pages.
European Search Report (partial) for EP App. No. 17873643.5 dated Jun. 3, 2020, 28 pages.
Granot et al., "Delivering the right message: Challenges and opportunities in lipid nanoparticles-mediated modified mRNA therapeutics—An innate immune system standpoint", *Seminars in Immunology*, 34, 2017, 68-77.
Hasan et al. "Injectable Hydrogels for Cardiac Tissue Repair after Myocardial Infarction", *Advanced Science*, 2015, 2 1500122, 1-18.
Hastings et al., "Drug and cell delivery for cardiac regeneration", Aug. 24, 2014, *Advanced Drug Delivery Reviews*, vol. 84, p. 85-106.
Huang et al., "Synthetic Chemically Modified mRNA-Based Delivery of Cytoprotective Factor Promotes Early Cardiomyocyte Survival Post-Acute Myocardial Infarction", Jan. 27, 2015, *Molecular Pharmaceutics*, 12(3), p. 991-996.
International Preliminary Report on Patentability for PCT/US17/63060 dated May 28, 2019, 12 pages.
International Search Report and Written Opinion of PCT/US17/63060 dated May 16, 2018, 16 pages.
Krebs et al., "Localized and Sustained Delivery of Silencing RNA from Macroscopic Biopolymer Hydrogels", Jul. 8, 2009, *Journal of the American Chemical Society*, vol. 131, No. 26, pp. 9204-9206.
Loyer et al., "Microvesicles as Cell-Cell Messengers in Cardiovascular Diseases", *Circulation Research*, 2014, 345-353.
Mozaffarian et al., "Heart Disease and Stroke Statistics—2015 update: a report from the American Heart Association", 2015, *Circulation*, 131(4):e29-322.
Partial European Search Report for EP Appl. No. 21205388.8 dated Feb. 11, 2022, 36 pages.
Petroni et al., "Primary percutaneous coronary intervention for ST elevation myocardial infarction in nanogenarians", 2016, *Heart*, vol. 102, p. 1648-1654.
Singh et al., "M 3 RNA Drives Targeted Gene Delivery in Acute Myocardial Infarction", Jan. 1, 2019, *Tissue Engineering Part A*, vol. 25, No. 1-2, p. 145-158.
Tavernier et al., "mRNA as gene therapeutic: How to control protein expression", *Journal of Controlled Release*, 150 (2011) 238-247.
Turnbull et al., "Myocardial Delivery of Lipidoid Nanoparticle mRNA Designed for Tailored Expression of Cardiogenic Factors", Nov. 1, 2013, *Circulation, American Heart Association*, vol. 128, No. 22.
Turnbull et al., "Myocardial Delivery of Lipidoid Nanoparticle Carrying modRNA Induces Rapid and Transient Expression", Jan. 1, 2016, *J. of the American Society of Gene Therapy*, vol. 24(1), p. 66-75.
Ustundag et al., "Comparative diagnostic accuracy of serum levels of neutrophil activating peptide-2 and pentraxin-3 versus troponin-I in acute coronary syndrome" 2011, *Anadolu Kardiyol Derg*, vol. 11(7), p. 588-94.
Wadhwa et al., "Opportunities and Challenges in the Delivery of mRNA-Based Vaccines", *Pharmaceutics*, 2020 12, 102, 1-27.
Nisisako et al., "Synthesis of Monodisperse Bicolored Janus Particles with Electrical Anisotropy Using a Microfluidic Co-Flow System**" 2006, Adv. Mater., 18:1152-1156.

* cited by examiner

A.

B.

C.

A.

B.

C.

A

B

C

SEQUENCE LISTING

<160> NUMBER OF SEQ ID NOS: 10

<210> SEQ ID NO 1
<211> LENGTH: 70
<212> TYPE: DNA
<213> ORGANISM: Artificial Sequence
<220> FEATURE:
<223> OTHER INFORMATION: Internal ribosome entry site

<400> SEQUENCE: 1
cccattgtat gggatctgat ctggggcctc ggtgcacatg ctttacatgt gtttagtcga    60
ggttaaaaaa                                                          70

<210> SEQ ID NO 2
<211> LENGTH: 47
<212> TYPE: DNA
<213> ORGANISM: Artificial Sequence
<220> FEATURE:
<223> OTHER INFORMATION: Internal ribosome entry site

<400> SEQUENCE: 2
acgtctaggc cccccgaacc acggggacgt ggttttcctt tgaaaaa                 47

<210> SEQ ID NO 3
<211> LENGTH: 138
<212> TYPE: DNA
<213> ORGANISM: Artificial Sequence
<220> FEATURE:
<223> OTHER INFORMATION: Internal ribosome entry site

<400> SEQUENCE: 3
ccagaaggta cccattgta tggatctga tctggggcct cggtacacat gctttacatg     60
tgtttagtcg aggttaaaaa aacgtctagg ccccccgaac cacggggacg tggttttcct   120
ttgaaaaaca cgatgata                                                138

<210> SEQ ID NO 4
<211> LENGTH: 173
<212> TYPE: DNA
<213> ORGANISM: Artificial Sequence
<220> FEATURE:
<223> OTHER INFORMATION: Internal ribosome entry site

<400> SEQUENCE: 4

```
atatggccac aaccatggtg agcaagggcg aggagctgtt caccggggtg gtgcccatcc      60
tggtcgagct ggacggcgac gtaaacggcc acaagttcag cgtgtccggc gagggcgagg     120
gcgatgccac ctacggcaag ctgaccctga agttcatctg caccaccggc aag            173
```

<210> SEQ ID NO 5
<211> LENGTH: 265
<212> TYPE: DNA
<213> ORGANISM: Artificial Sequence
<220> FEATURE:
<223> OTHER INFORMATION: Internal ribosome entry site
<220> FEATURE:
<221> NAME/KEY: misc_feature
<222> LOCATION: (26)..(26)
<223> OTHER INFORMATION: n is a, c, g, or t
<220> FEATURE:
<221> NAME/KEY: misc_feature
<222> LOCATION: (30)..(30)
<223> OTHER INFORMATION: n is a, c, g, or t
<220> FEATURE:
<221> NAME/KEY: misc_feature
<222> LOCATION: (167)..(169)
<223> OTHER INFORMATION: n is a, c, g, or t
<220> FEATURE:
<221> NAME/KEY: misc_feature
<222> LOCATION: (187)..(188)
<223> OTHER INFORMATION: n is a, c, g, or t
<220> FEATURE:
<221> NAME/KEY: misc_feature
<222> LOCATION: (197)..(199)
<223> OTHER INFORMATION: n is a, c, g, or t
<220> FEATURE:
<221> NAME/KEY: misc_feature
<222> LOCATION: (204)..(215)
<223> OTHER INFORMATION: n is a, c, g, or t

<400> SEQUENCE: 5

```
gctgctgccc gacaaccact acctgnagcn acccagtccg ccctgagcaa agaccccaac      60
gagaagcgcg atcacatggt cctgctggag ttcgtgaccg ccgccgggat cactctcggc     120
atggacgagc tgtacaagta agccctgtgg aatgtgtgtc agttagnnng gtgtggaaag     180
tccccanngg ctccccnnna gcannnnnnn nnnnnggcag aagtatgcaa agcatgcatc     240
tcaattagtc agcaaccagg tgtgg                                            265
```

<210> SEQ ID NO 6
<211> LENGTH: 160
<212> TYPE: DNA
<213> ORGANISM: Artificial Sequence
<220> FEATURE:
<223> OTHER INFORMATION: Internal ribosome entry site
<220> FEATURE:
<221> NAME/KEY: misc_feature
<222> LOCATION: (41)..(43)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t

<400> SEQUENCE: 6
caacgtctat atcatggccg acaagcagaa gaacggcatc nnnaaggtga acttcaagat      60
ccgccacaac atcgaggacg gcagcgtgca gctcgccgac cactaccagc agaacacccc     120
catcnggcga cggccccgtg ctgctgcnnc cgacaaccac                           160

<210> SEQ ID NO 7
<211> LENGTH: 160
<212> TYPE: DNA
<213> ORGANISM: Artificial Sequence
<220> FEATURE:
<223> OTHER INFORMATION: Internal ribosome entry site
<220> FEATURE:
<221> NAME/KEY: misc_feature
<222> LOCATION: (41)..(43)
<223> OTHER INFORMATION: n is a, c, g, or t
<220> FEATURE:
<221> NAME/KEY: misc_feature
<222> LOCATION: (125)..(125)
<223> OTHER INFORMATION: n is a, c, g, or t
<220> FEATURE:
<221> NAME/KEY: misc_feature
<222> LOCATION: (148)..(149)
<223> OTHER INFORMATION: n is a, c, g, or t

<400> SEQUENCE: 7
caacgtctat atcatggccg acaagcagaa gaacggcatc nnnaaggtga acttcaagat      60
ccgccacaac atcgaggacg gcagcgtgca gctcgccgac cactaccagc agaacacccc     120
catcnggcga cggccccgtg ctgctgcnnc cgacaaccac                           160

<210> SEQ ID NO 8
<211> LENGTH: 136
<212> TYPE: DNA
<213> ORGANISM: Artificial Sequence
<220> FEATURE:
<223> OTHER INFORMATION: Internal ribosome entry site
<220> FEATURE:
<221> NAME/KEY: misc_feature
<222> LOCATION: (28)..(29)
<223> OTHER INFORMATION: n is a, c, g, or t
<220> FEATURE:
<221> NAME/KEY: misc_feature
<222> LOCATION: (56)..(56)
<223> OTHER INFORMATION: n is a, c, g, or t
<220> FEATURE:
<221> NAME/KEY: misc_feature
<222> LOCATION: (95)..(97)
<223> OTHER INFORMATION: n is a, c, g, or t
<220> FEATURE:
<221> NAME/KEY: misc_feature
<222> LOCATION: (119)..(121)
<223> OTHER INFORMATION: n is a, c, g, or t

<400> SEQUENCE: 8
gctgaagcac tgcacgccgt aggtcagnng gtggtcacga gggtgggcca gggcancggg      60
cagcttgccg gtggtgcaga tgaacttcag ggtcnnnagc ttgccgtagg tggcatcgnn     120
nccctcgccc tcgccg                                                      136

<210> SEQ ID NO 9
<211> LENGTH: 235
<212> TYPE: DNA
<213> ORGANISM: Artificial Sequence
<220> FEATURE:
<223> OTHER INFORMATION: Internal ribosome entry site
<220> FEATURE:
<221> NAME/KEY: misc_feature
<222> LOCATION: (55)..(57)

<223> OTHER INFORMATION: n is a, c, g, or t
<220> FEATURE:
<221> NAME/KEY: misc_feature
<222> LOCATION: (94)..(96)
<223> OTHER INFORMATION: n is a, c, g, or t
<220> FEATURE:
<221> NAME/KEY: misc_feature
<222> LOCATION: (194)..(194)
<223> OTHER INFORMATION: n is a, c, g, or t

<400> SEQUENCE: 9

```
gacacgctga acttgtggcc gtttacgtcg ccgtccagct cgaccaggat gggcnnnacc     60
accccggtga acagctcctc gcccttgctc accnnnatgg ttgtggccat attatcatcg    120
tgtttttcaa aggaaaacca cgtccccgtg gttcgggggg cctagacgtt tttttaacct    180
cgactaaaca catngtaaag catgtgtacc gaggccccag atcagatccc ataca         235
```

<210> SEQ ID NO 10
<211> LENGTH: 389
<212> TYPE: DNA
<213> ORGANISM: Artificial Sequence
<220> FEATURE:
<223> OTHER INFORMATION: Internal ribosome entry site
<220> FEATURE:
<221> NAME/KEY: misc_feature
<222> LOCATION: (80)..(82)
<223> OTHER INFORMATION: n is a, c, g, or t
<220> FEATURE:
<221> NAME/KEY: misc_feature
<222> LOCATION: (101)..(106)
<223> OTHER INFORMATION: n is a, c, g, or t
<220> FEATURE:
<221> NAME/KEY: misc_feature
<222> LOCATION: (126)..(133)
<223> OTHER INFORMATION: n is a, c, g, or t
<220> FEATURE:
<221> NAME/KEY: misc_feature
<222> LOCATION: (138)..(146)
<223> OTHER INFORMATION: n is a, c, g, or t
<220> FEATURE:
<221> NAME/KEY: misc_feature
<222> LOCATION: (175)..(176)
<223> OTHER INFORMATION: n is a, c, g, or t
<220> FEATURE:
<221> NAME/KEY: misc_feature
<222> LOCATION: (201)..(201)
<223> OTHER INFORMATION: n is a, c, g, or t
<220> FEATURE:
<221> NAME/KEY: misc_feature
<222> LOCATION: (205)..(209)
<223> OTHER INFORMATION: n is a, c, g, or t
<220> FEATURE:
<221> NAME/KEY: misc_feature
<222> LOCATION: (234)..(243)
<223> OTHER INFORMATION: n is a, c, g, or t
<220> FEATURE:
<221> NAME/KEY: misc_feature
<222> LOCATION: (252)..(255)
<223> OTHER INFORMATION: n is a, c, g, or t
<220> FEATURE:
<221> NAME/KEY: misc_feature
<222> LOCATION: (264)..(264)
<223> OTHER INFORMATION: n is a, c, g, or t
<220> FEATURE:
<221> NAME/KEY: misc_feature
<222> LOCATION: (270)..(270)
<223> OTHER INFORMATION: n is a, c, g, or t
<220> FEATURE:
<221> NAME/KEY: misc_feature
<222> LOCATION: (313)..(316)
<223> OTHER INFORMATION: n is a, c, g, or t
<220> FEATURE:
<221> NAME/KEY: misc_feature
<222> LOCATION: (343)..(353)
<223> OTHER INFORMATION: n is a, c, g, or t

```
<400> SEQUENCE: 10
agggcacggg cagcttgccg gtggtgcaga tgaacttcag ggtcagcttg ccgtaggtgg      60
catcgccctc gccctcgccn nnggacacgc tgaacttgtg nnnnnngccg tttacgtcgc     120
cgtccnnnnn nnnagctnnn nnnnnncgac caggatgggc accacccgg tgaanncagc      180 tcctcgccct tgctcaccat nggtnnnnnt gtggccatat tatcatcgtg tttnnnnnnn    240
nnnttcaaag gnnnnaaaac cacngtcccn cgtggttcgg ggggcctaga cgttttttta     300
acctcgacta aannnncaca tgtaaagcat gtgtaccgag gcnnnnnnnn nnncccagat     360
cagatcccat acaatggggt accttctgg                                       389
```

PARTICLE-MEDIATED DELIVERY OF BIOLOGICS

CROSS-REFERENCE TO RELATED APPLICATIONS

This application is a continuation of U.S. patent application Ser. No. 16/463,053 filed May 22, 2019, which is the § 371 U.S. National Stage of International Application No. PCT/US2017/063060, filed Nov. 22, 2017, which claims priority to U.S. Provisional Patent Application No. 62/426,090, filed Nov. 23, 2016, each of which is incorporated herein by reference in its entirety.

SEQUENCE LISTING

This application contains a Sequence Listing electronically submitted via EFS-Web to the United States Patent and Trademark Office as an ASCII text file entitled "560000004US02_ST25.txt" having a size of 7 kilobytes and created on May 22, 2019. The information contained in the Sequence Listing is incorporated by reference herein.

BACKGROUND

A heart attack, also called a myocardial infarction, occurs when a part of the heart muscle does not receive enough blood flow. The more time that passes without treatment to restore blood flow, the greater the damage to the heart muscle. Every year, about 735,000 Americans have a heart attack, including about 210,000 heart attacks that happen to people who have already had a first heart attack (Mozaffarian et al., Circulation, 131(4):e29-322 (2015)).

SUMMARY

This disclosure describes modifications to RNA molecules that increase the length of time that the modified RNA molecules exist in cells.

This disclosure further provides materials and methods for particle-mediated delivery of one or more biologics (e.g., RNA, modified RNA, and/or microvesicles) to a tissue (e.g., heart tissue). Microvesicles can represent manufactured particles or naturally occurring structures, such as exosomes. For example, this document provides particles (e.g., alginate gels) for delivering one or more RNAs to cardiac tissue to improve cardiac function.

As demonstrated herein, an alginate gel can be used to deliver mRNA to a heart tissue where the mRNA can be translated into a functional polypeptide. Particle-mediated delivery of RNA can induce robust and sustainable RNA expression. In some cases, particles can be used be designed to control temporal and/or spatial delivery of one or more encapsulated molecules (e.g., biologics).

In one aspect, therefore, this disclosure describes composition that generally include a particulate substrate and an mRNA attached to the particulate substrate. The mRNA includes at least one modification to inhibit degradation of the mRNA when the mRNA is in cytosol of a cell. The mRNA also encodes at least one therapeutic polypeptide. In some embodiments, the mRNA modification comprises a pseudoknot, an RNA stability element, or an artificial 3' stem loop. In some embodiments, the particulate substrate can include a chemical modification of its surface. In various embodiments, the particulate substrate can include a nanoparticle, a plurality of nanoparticles, or a microparticle. In some embodiments, the therapeutic polypeptide can include an immunoglobulin heavy chain or an immunoglobulin light chain.

In general, one aspect of this document features a method for improving cardiac function. The method includes, or consists essentially of, administering a particle encapsulating an mRNA encoding a polypeptide useful for regenerating cardiac function and/or tissue to a mammal, thereby improving cardiac function of the mammal. The polypeptide can be NAP-2, TGF-a, ErBb3, VEGF, IGF-1, FGF-2, PDGF, IL-2, CD19, CD20, and/or CD80/86. The mammal can be a human. The human can have undergone percutaneous coronary intervention for ST-elevation myocardial infarction. The administering can be an arterial administration. The particle can include alginate. The alginate can be in the form of an alginate gel. The alginate gel can include a calcium salt. The alginate gel including a calcium salt can have a ratio of alginate to calcium salt that can be from about 2:1 to about 10:1. The particle can be from about 5 μm to about 10 μm in diameter. The particle can be a biphasic particle. The biphasic particle can be a polarized particle. The biphasic particle can have a tail. The method can include administering the composition during a percutaneous coronary intervention. The particle can include a scaffold protein (e.g., collagen I, collagen II, collagen III, collagen IV, fibrin, and/or gelatin). The particle can encapsulate a polypeptide (e.g., an antibody having the ability to neutralize tumor necrosis factor activity, an antibody having the ability to neutralize mitochondrial complex-1 activity, or a resolvin-D1 agonist). The particle can encapsulate a lipopolysaccharide. The particle can encapsulate a microvesicle and/or exosome.

In another aspect, this document features a method for improving cardiac function in a mammal. The method includes, or consists essentially of, administering to a mammal a particle encapsulating an inhibitory RNA having the ability to reduce expression of a polypeptide selected from the group consisting of eotaxin-3, cathepsin-S, DK-1, follistatin, ST-2, GRO-a, IL-21, NOV, transferrin, TIMP-2, TNFaRI, TNFaRII, angiostatin, CCL25, ANGPTL4, and MMP-3, thereby improving cardiac function of the mammal. The mammal can be a human. The human can have undergone percutaneous coronary intervention for ST-elevation myocardial infarction. The administering can be an arterial administration. The particle can include alginate. The alginate can be in the form of an alginate gel. The alginate gel can include a calcium salt. The alginate gel including a calcium salt can have a ratio of alginate to calcium salt that can be from about 2:1 to about 10:1. The particle can be from about 5 μm to about 10 μm in diameter. The particle can be a biphasic particle. The biphasic particle can be a polarized particle. The biphasic particle can include a tail. The method can include administering the composition during a percutaneous coronary intervention. The particle can include a scaffold protein (e.g., collagen I, collagen II, collagen III, collagen IV, fibrin, and/or gelatin). The particle can encapsulate a polypeptide (e.g., an antibody having the ability to neutralize tumor necrosis factor activity, an antibody having the ability to neutralize mitochondrial complex-1 activity, or a resolvin-D1 agonist). The particle can encapsulate a lipopolysaccharide. The particle can encapsulate a microvesicle and/or exosome.

Unless otherwise defined, all technical and scientific terms used herein have the same meaning as commonly understood by one of ordinary skill in the art to which this disclosure belongs. Methods and materials are described herein for use in the present disclosure; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

The details of one or more embodiments of the invention are set forth in the accompanying drawings and the description below. Other features, objects, and advantages of the invention will be apparent from the description and drawings, and from the claims.

DETAILED DESCRIPTION OF EXEMPLARY EMBODIMENTS

Figure 1:
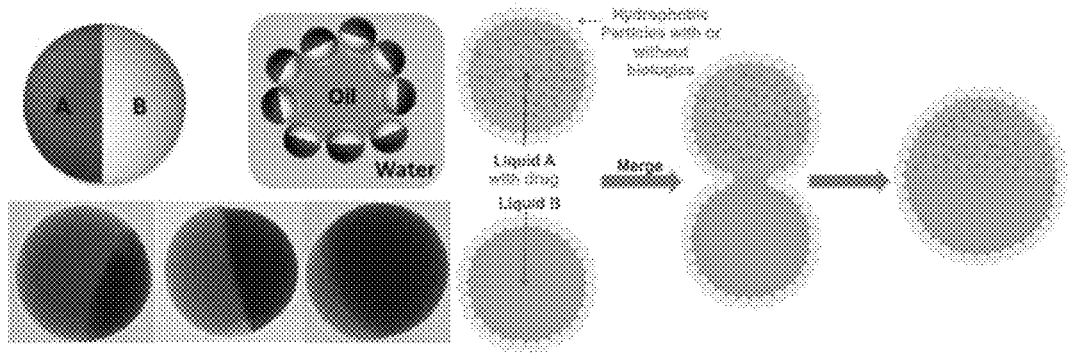
FIG. 1 Schematics illustrations of exemplary methods for making biphasic particles. (A) A stabilizer technology method where two separate soft liquid cores, such as a water-based component and an oil-based component, are stabilized and then merged into a single Janus particle. (B) A melt combination and fusion method where two polymer streams are merged together forming a single particle and cooled to form two hemispheres of a Janus particle. (C) A microfluidics method that uses controlled liquid flow in microfluidic channels to form droplets that are solidified into formed Janus particles.
Figure 1:
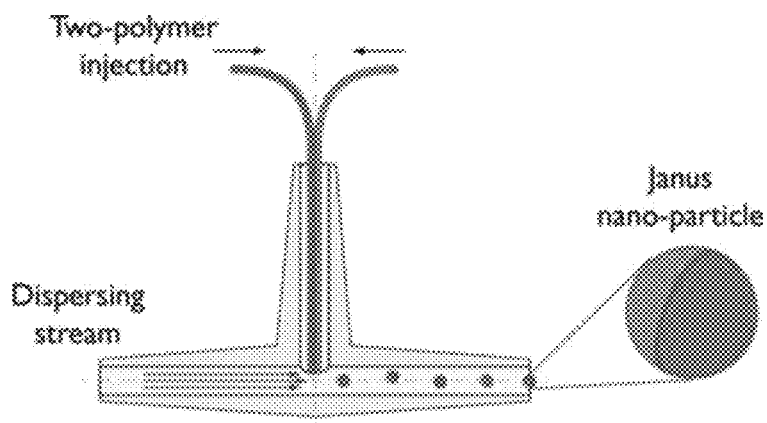
Figure 1:
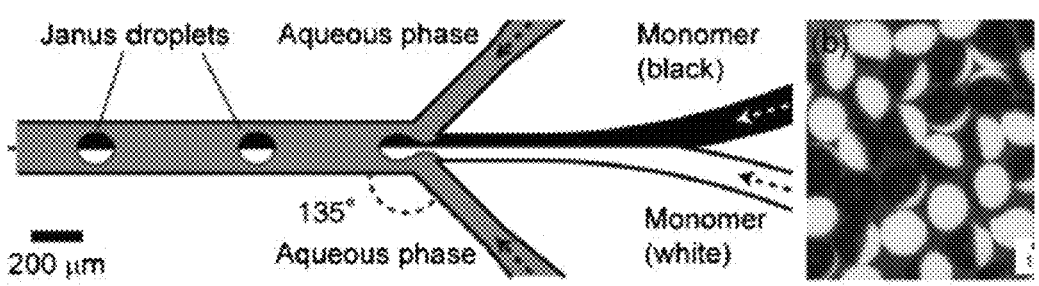

This disclosure relates to materials and methods for particle-mediated delivery of biologics (e.g., RNA and/or microvesicles) to tissue (e.g., heart tissue). This disclosure further describes modifications to RNA that increase the length of time that the modified mRNA molecules exist in cells and, therefore, the length of time that the modified mRNA molecules can be translated into produce polypeptides encoded by the modified mRNA.

This disclosure provides materials and methods for particle-mediated delivery of one or more biologics (e.g., RNA and/or microvesicles) to a mammal. For example, a particle (e.g., an alginate gel) described herein can be used to encapsulate RNA and deliver the encapsulated RNA to a tissue in a temporally and/or spatially specific manner. As used herein, the term "encapsulate" and variations thereof is used broadly to refer to any method by which a biologic is housed within a particle or bound, directly or indirectly, to the outer surface of a particle. As explained in more detail below, the particle can be nanoparticulate or microparticulate in scale. Thus, the term "encapsulate" includes, but does not require, that the particle completely surround the material being encapsulated. Rather, a material is encapsulated if it is merely captured to any degree within the dimensions of the particle, including any surface modifications. Surface modifications of the particle can facilitate indirect binding of the encapsulated material to the particle. In addition, macroencapsulation can be used to deliver a biologic by providing a protective vehicle by which to transmit the biologics either by direct injection or through a blood vessel into a target tissue.

In some cases, one or more particles (e.g., alginate gels) containing one or more biologics (e.g., RNAs and/or microvesicles) can be used to treat a mammal experiencing a major adverse cardiac event (e.g., acute myocardial infarction) and/or a mammal at risk of experiencing a major adverse cardiac event (e.g., patients who underwent percutaneous intra intervention (PCI) for ST-elevation myocardial infarction (STEMI)).

In some cases, one or more particles (e.g., an alginate gels) containing one or more biologics (e.g., RNAs or microvesicles) can be used to improve cardiac function.

In some cases, a particle (e.g., an alginate gel) described herein can store mRNA within its interior, and release (e.g., deliver) the mRNA to a tissue (e.g., heart tissue) where the mRNA is expressed as a functional protein. For example, one or more particles containing one or more mRNAs can be used to increase expression of polypeptides useful for regenerating cardiac function and/or tissue (e.g., POU homeodomain proteins (such as Oct-4), NK2 homeobox proteins (e.g., NKX2 proteins), myocyte enhancing factors (e.g., MEF2), GATA binding proteins (e.g., GATA1, GATA2, GATA3, GATA4, GATA5, and GATA6), T-box transcription factors (e.g., TBX1, TBX2, TBX3, TBX4, TBX5, TBX6, TBX10, TBX15, TBX18, TBX19, TBX20, TBX21, and TBX22), mesoderm posterior proteins (e.g., MESP1 and MESP2), neutrophil-activating proteins (e.g., NAP-2 and NAP-3), transforming growth factors (e.g., TGF-α and TGF-β), erythroblastic leukemia viral oncogene-3 (ErBb3), vascular endothelial growth factor (VEGF), insulin-like growth factor 1 (IGF-1), fibroblast growth factor (FGF-2), platelet-derived growth factors (e.g., PDGFA, PDGFB, PDGFC, and PDGFD), Interleukin-2 (IL-2), CD19, CD20, and CD80/86).

In some cases, a particle (e.g., an alginate gel) described herein can store inhibitory RNA within its interior, and release (e.g., deliver) the inhibitory RNA to a tissue (e.g., heart tissue) where the inhibitory RNA inhibits or reduces expression of a protein. For example, one or more particles containing one or more inhibitory RNAs can be used to decrease expression of one or more of the following polypeptides: eotaxin-3, cathepsin-S, Dickopf-1 (DK-1), follistatin, suppression of tumorigenicity-2 (ST-2), GRO-α, interleukin-21 (IL-21), nephroblastoma overexpressed (NOV), transferrin, tissue inhibitor of metallopeptidase-2 (TIMP-2), tumor necrosis factor receptor-1 and -2 (TNFαRI and II), angiostatin, chemokine ligand-25 (CCL25), angiopoietin like-4 (ANGPTL4), and matrix metalloproteinase-3 (MMP-3).

Particles

A particle described herein can be used for particle-mediated delivery of one or more molecules (e.g., biologics including RNA or microvesicles) to a mammal. In some cases, a particle that can be used to encapsulate one or more biologics is non-toxic, biocompatible, non-immunogenic, and/or biodegradable.

A particle that can be used to encapsulate one or more biologics as described herein can include one or more polysaccharides. Examples of polysaccharides that can be used in a particle that can be used to encapsulate one or more molecules (e.g., biologics) as described herein include, for example, guluronate, mannuronate, guluronate-mannuronate blocks, and combinations thereof such as alginate. In some cases, a particle that can be used to encapsulate one or more biologics as described herein can include alginate. An alginate in a particle that can be used to encapsulate one or more biologics as described herein can be from any appropriate source (e.g., seaweeds such as those in the genera *Phaeophyceae*, *Rhodophyceae*, *Chlorophyceae*, *Macrocystis*, and *Laminaria*, or bacteria such as those in the genera *Pseudomonas* and *Azotobacter*). An alginate in a particle that can be used to encapsulate one or more biologics as described herein can be an alginate salt (e.g., sodium alginate, potassium alginate, and/or calcium alginate) or alginic acid. For example, an alginate in a particle that can be used to encapsulate one or more biologics as described herein can be sodium alginate. An alginate in a particle that can be used to encapsulate one or more biologics as described herein can be in the form of a gel, a liquid, and/or a particle (e.g., a nanoparticle, a microparticle, or a macroparticle). For example, an alginate in a particle that can be used to encapsulate one or more biologics as described herein can be an alginate gel. In some cases, a particle described herein can be a liquid at the time of administration and can form a gel (e.g., can polymerize) at the administration site and/or the target site. An alginate gel can include a calcium solution (e.g., a calcium salt solution or another appropriate positively charged ionic solution). Examples of calcium salts that can be used in a calcium solution to form an alginate gel that can be used to encapsulate one or more biologics as described herein include, without limitation, calcium chloride, magnesium chloride, potassium chloride, and iron-based solutions. The ratio of alginate to calcium salt can be used to control the viscosity of the alginate gel that can be used to encapsulate one or more biologics as described herein. In some cases, the amount of alginate can be from about 0.05 percent to about 1.0 percent of the amount of calcium salt. In some cases, the ratio of alginate to calcium salt can be can be from about 2:1 to about 10:1 (e.g., from about 2:1 to about 9:1, from about 2:1 to about 8:1, from about 2:1 to about 7:1, from about 2:1 to about 6:1, from about 2:1 to about 5:1, from about 3:1 to about 10:1, from about 4:1 to about 10:1, from about 5:1 to about 10:1, from about 6:1 to about 10:1, from about 7:1 to about 10:1, or from about 8:1 to about 10:1). Examples of appropriate alginate/calcium ratios include, without limitation, those set forth in Table 1. An alginate gel encapsulating a biologic (e.g., mRNA) described herein can be made by any appropriate method. For example, an alginate gel can be made by hydrolyzing an alginate salt (e.g., sodium alginate) using a soluble calcium salt solution (e.g., calcium chloride) as a crosslinking agent.

TABLE 1

Examples alginate/calcium concentrations.

| alginate concentration | calcium concentration | alginate:calcium |
|---|---|---|
| 0.2% | 0.1% | 2:1 |
| 1% | 0.1% | 10:1 |
| 2% | 0.5% | 4:1 |
| 2% | 0.25% | 8:1 |

A particle that can be used to encapsulate one or more biologics as described herein can be in the form of a liposome, an aggregate (e.g., a nano-aggregate), a capsule (e.g., a nanocapsule), a sphere (e.g., a nanosphere), a polymersome, or a micelle. A particle that can be used to encapsulate one or more biologics as described herein that is an alginate gel can be in the form of polymerized sphere. In some cases, a particle that can be used to encapsulate one or more biologics as described herein can be a liposome. Examples of liposomes include, without limitation, a multilamellar vesicle (MLV), a small unilamellar liposome vesicle (SUV), a large unilamellar vesicle (LUV), a giant unilamellar vesicle (GUV), a multivesicular vesicles (MVV), or a cochleate vesicle. A liposome can be composed of phospholipids, cholesterols, lipoproteins, fats, fatty acids, waxes, sterols, monoglycerides, diglycerides, and/or triglycerides. In some cases, a liposome is composed of phospholipids such as phosphatidic acid (phosphatidate; PA), phosphatidylethanolamine (cephalin; PE), phosphatidylcholine (lecithin; PC), phosphatidylserine (PS), phosphoinositides (e.g., phosphatidylinositol (PI), phosphatidylinositol phosphate (PIP), phosphatidylinositol bisphosphate (PIP2), and phosphatidylinositol triphosphate (PIP3)), ceramide phosphorylcholine (sphingomyelin; SPH), ceramide phosphorylethanolamine (sphingomyelin; Cer-PE), ceramide phosphoryllipid, or any combination thereof. Examples of appropriate liposomes include, without limitation, those set forth in Table 2. A liposome encapsulating a biologic (e.g., mRNA) described herein can be made by any appropriate method. For example, a liposome can be made by sonicating a dispersion of amphipatic lipids, such as phospholipids, in water.

TABLE 2

Examples of liposome components.

| liposome component | MW (kDa) | Concentration |
|---|---|---|
| Charged Poly(lactide-co-glycolide) (PLGA) | about 46 | 3-300 mg |
| 1,2-Dioleoyl-sn-glycero-3-phosphoethanolamine (DOPE) | about 744 | 20 µg-1 mg |
| N-[1-(2,3-dioleoyloxy)propyl]-N,N,N-trimethylammonium methylsulfate (DOTAP) | about 774 | 20 µg-3 mg |
| L-α-Phosphatidylethanolamine, dioleoyl | about 744 | 20 µg-3 mg |

TABLE 2-continued

Examples of liposome components.

| liposome component | MW (kDa) | Concentration |
|---|---|---|
| 1,2-Distearoyl-sn-glycero-3-phosphoethanolamine-Poly(ethylene glycol) (DSPE- PEG) | about 770 | 20 µg-3 mg |
| Poly(vinyl-alcohol) (PVA) | about 78 | 1-5% per total volume |

A particle that can be used to encapsulate one or more biologics as described herein can be any size suitable for the selected delivery method. A particle that can be used to encapsulate one or more biologics as described herein can be from about 0.3 µm to about 12 µm (e.g., from about 0.5 µm to about 11.5 µm, from about 1 µm to about 11 µm, from about 2 µm to about 10.5 µm, or from about 4 µm to about 10 µm) in diameter (or as measure across the longest dimension). For example, a particle that can be used to encapsulate one or more biologics as described herein can be from about 4.5 µm to about 7.5 µm in diameter (or as measure across the longest dimension).

A particle (e.g., an alginate gel) encapsulating one or more biologics described herein also can include one or more additional molecules in order to achieve a desired property. In some cases, a particle encapsulating one or more biologics described herein can include one or more scaffold proteins. Examples of scaffold proteins include, for example, matrix proteins (e.g., collagen (e.g., collagen I/II/III/IV)), basement membrane proteins, structural proteins, gelatin, and/or fibrin) can be incorporated into a particle to provide the particle with sustained release properties. For example, an alginate gel encapsulating one or more biologics described herein can include alginate and gelatin, alginate and collagen, alginate and fibrin, or any other appropriate combination of alginate with one or more natural basement membrane proteins. In some cases, stimuli-sensitive molecules can be incorporated into a particle to provide the particle with drug release properties under specific stimuli (e.g., pH-sensitive particles and osmolarity/osmolality sensitive particles). For example, dioleoylphosphatidylethanolamine (DOPE) can be incorporated into a particle to provide a pH-sensitive particle that maintains stability at physiological pH (about pH 7.4), but destabilize under acidic conditions (e.g., about pH 3.5 to about pH 9) leading to the release of the encapsulated RNA in acidic environments.

A particle (e.g., an alginate gel) encapsulating one or more biologics described herein can be an amorphous particle having two or more distinct physical states. For example, an amorphous particle can be administered as a liquid and form a gel upon arriving at a target tissue.

A particle (e.g., an alginate gel) encapsulating one or more biologics described herein can be a biphasic particle (sometimes referred to as a Janus particle) having two or more distinct physical properties (e.g., surface chemistry) occurring on different portions of the particle surface. For example, a biphasic particle can have two or more portions that differ in hydrophilic/hydrophobic properties, polarization, solubility properties, volume percent or density of the particle composition, the presence/absence of an additional molecule (e.g., a compound providing sustained release properties), and/or the presence/absence of a tail. In some cases, a biphasic particle can be a spherical particle having hydrophilic portions and hydrophobic portions. For example, a biphasic particle can be designed to have a hydrophilic core and a hydrophilic coating. For example, a biphasic particle can be designed to have a hydrophilic core and a hydrophilic coating. In some cases, a biphasic particle can be a spherical particle having differential density. For example, a biphasic particle can be designed to have increased volume percent of an encapsulated biologic at one end of the particle. In some cases, a biphasic particle can be a spherical particle having a coating. For example, a biphasic particle can be designed to have a porous coating. In some cases, a biphasic particle can be a spherical particle having differential solubility. For example, a biphasic particle can be designed to have a first side that readily dissolves in certain physiological conditions and a second side that dissolves slowly in the same physiological conditions. In some cases, a biphasic particle can be a spherical particle having a tail extending from one portion of the particle surface. For example, a biphasic particle can be designed to guide particles in the blood flow. In some cases, a biphasic particle can be designed to have a first (e.g., leading) side that readily dissolves in certain physiological conditions and a second side that dissolves slowly in the same physiological conditions and includes a tail to guide particles in the blood flow.

A biphasic particle encapsulating one or more biologics described herein can be made using any appropriate method. In some cases, a biphasic particle can be made using stabilizer technology (e.g., including dry water approaches). For example, two or more separate soft liquid cores (e.g., two liquids having different hydrophobicity such as a hydrophobic entity and hydrophilic entity, or two liquids having different solubility such as water and an oil) can be stabilized and then merged into a biphasic particle. In some cases, a biphasic particle can be made using melt combination and fusion technology. For example, two or more separate streams (e.g., two streams of molten wax having differential properties, or two streams of polymers having different properties) can be merged (e.g., injected into a single stream) to form a biphasic particle. In some cases, a biphasic particle can be made using 3D-printer technology. For example, two or more coatings (e.g., two wax coatings having different properties) can be printed onto a particulate internal structural element (e.g., a particle of polystyrene foam such as STYROFOAM™) to form a biphasic particle. The particulate internal structural element can be removed (e.g., by acetone elimination) and replaced with one or more biologics. In some cases, a biphasic particle can be made using microfluidics technology. For example, two or more liquid flows (e.g., two liquids having different properties) can be flowed into a microfluidic channel to form biphasic droplets, which can be solidified (e.g., by thermal polymerization, elimination of sheer stress on spatially divalent particles, evaporation, coagulation, cation exposure, or pH) into biphasic particles. In some cases, a biphasic particle can be made using protection and de-protection technology. For example, a protection particle having a desired surface chemistry can be adsorbed onto a main particle; de-protection can yield the original surface of the main particle, which can be chemically modified.

In some cases, a biphasic particle can be made use other appropriate technologies. For example, other appropriate methods can include, without limitation, interfacial emulsification, acorn and dumbbell shaped formation, use of magnetic fields to shape and manipulate particles during fabrication, and direct surface coating deposition. In some embodiments, differential density can be achieved using organogels with varied density. In some embodiments, differential porosity can be achieved using salts at a particular surface of the particle. In some embodiments, differential solubility can be achieved using salts and/or using two or more different polymers (e.g., PEGs) having different solubilities. In some embodiments, various tails can be achieved using waxy components, chemically modifying (e.g., with long-chain reactants), and/or magnetizing a particle. Exemplary methods for making a biphasic particle encapsulating one or more biologics described herein are shown in FIG. 1.

Figure 14:
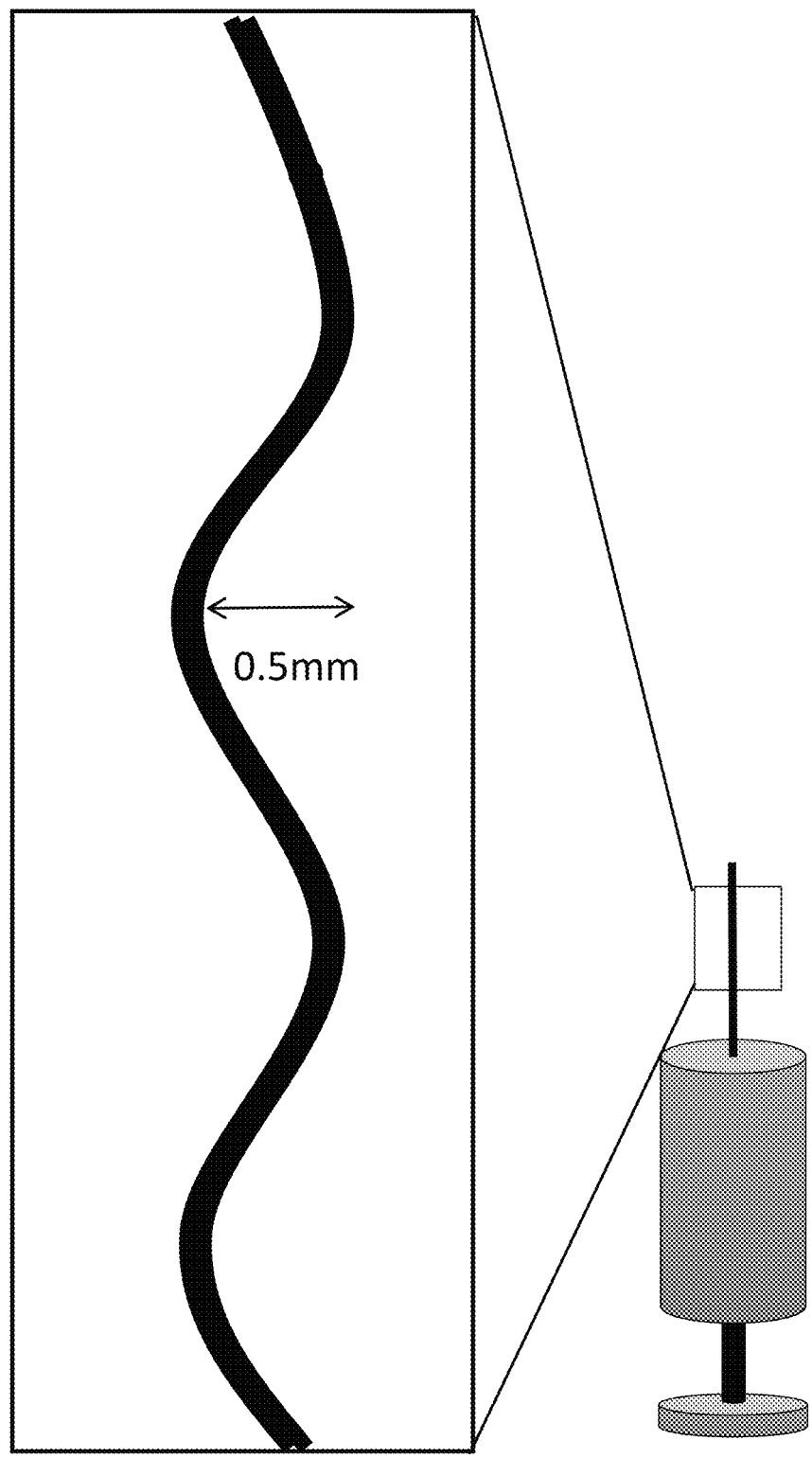
FIG. 14. A needle design for efficient biologics delivery into tissues, featuring a micro-spiral design and side holes.

A particle (e.g. an alginate gel) encapsulating one or more biologics described herein can be used to deliver the encapsulated biologics to a target tissue (e.g., heart tissue). Mechanisms of targeting a particle described herein can include using an adhesive particle, a targeting moiety, particle size, capillary leakage in the setting of injury, capillary leakage in the setting of oncogenic neovasculogenesis, and/or direct injection (e.g., via an edema forming needle (e.g., a nitinol (nickel-titanium) helical needle) designed with graded side holes and no end hole (see, e.g., FIG. 14)). Capillary leakage refers to any physical, chemical, or pharmacological means by which one can enhance capillary porosity or leakage in order to augment biologics delivery. This can be achieved either by administering a factor (e.g., chemical and/or pharmacologic) that enhances capillary porosity. Alternatively, capillary leakage may be achieved by placing a biologics delivery needle that is designed to mimic edema into the target tissue.

Figure 2:
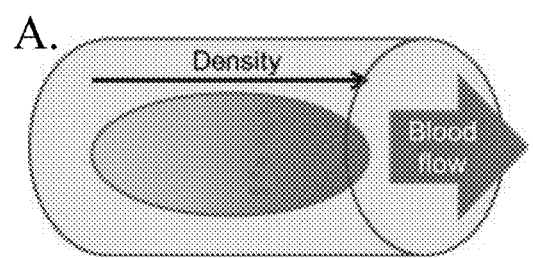
FIG. 2. Schematic illustrations of exemplary delivery methods using biphasic particles. (A) A Janus particle with different volume percent or density could orient the particle within the blood flow and direct the biologics in an appropriate orientation for delivery. (B) A Janus particle having a coating can control the rate of release and/or augment orienting capability. (C) A Janus particle having a tail (top), having differential solubility (middle), and/or having differential positioning of microcapsules on either end of the Janus particle (bottom) can provide orienting guidance to the particle.
Figure 2:
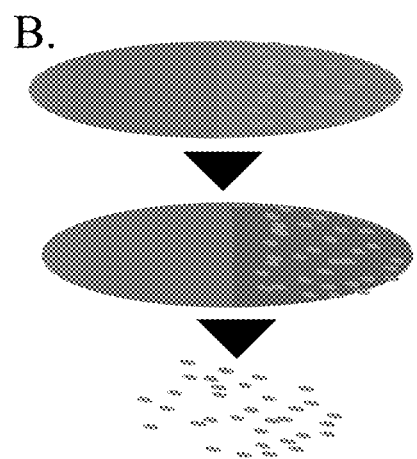
Figure 2:
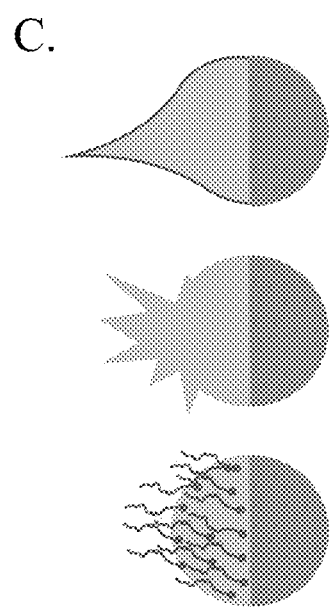

In some cases, an adhesive moiety can be conjugated to a particle described herein to retain an adhesive particle at the administration site. For example, an adhesive particle described herein can be administered (e.g., injected) directly to a target tissue (e.g., cardiac infarct bed). Examples of adhesive moieties include, without limitation, PEG, positive charge, and self-assembly within tissue. In some cases, a targeting moiety can be conjugated to a particle described herein to direct delivery of a particle to a target tissue (e.g., cardiac infarct bed). Examples of targeting moieties include, without limitation, antigens, tissue targeting peptides, small molecules, and cell surface molecules. For example, an antibody can be used to target surface proteins on a cell. In some cases, the size of the particle can be used to direct delivery of a particle to a target tissue (e.g., cardiac infarct bed). Human capillaries measure about 5 µm to 10 µm in diameter. Thus, a particle described herein having a diameter of from about 0.3 µm to about 12 µm can enter a capillary via the bloodstream, but be limited from exiting the capillary, where the biologics and/or an expressed polypeptide can diffuse into the capillary bed of a tissue (e.g., heart, dermal, lung, solid tumor, brain, bone, ligament, connective tissue structures, kidney, liver, subcutaneous, and vascular tissue). Exemplary methods for delivery of one or more biologics using a biphasic particle described herein are shown in FIG. 2.

A particle (e.g., an alginate gel) encapsulating one or more biologics described herein can be used to deliver the encapsulated biologic to a target tissue (e.g., cardiac infarct bed) in a temporally and/or spatially specific manner. For example, a biphasic particle encapsulating one or more biologics as described herein can be designed to confer a specific orientation of the particle within a blood vessel, to direct the biphasic particle into a capillary, and/or to confer specific release conditions of the encapsulated biologics. In cases where a biphasic particle has hydrophilic portions and hydrophobic portions on the particle surface, delivery of one or more encapsulated biologics can be controlled by the solvent present at the delivery site and/or the target site. In cases where a biphasic particle has differential density, the differential density can orient the particle in the blood flow to direct the particle in an appropriate orientation for delivery of one or more encapsulated biologics. For example, a dense side of a biphasic particle can lead the particle in the direction of blood flow within a blood vessel. In cases where a biphasic particle has a porous coating, delivery of one or more encapsulated biologics can be controlled by the differential porosity. For example, different amounts of porosity can help deliver particles within the blood vessel and alter the pattern of delivery. In cases where a biphasic particle has differential solubility, the differential solubility can orient the particle in the blood flow to direct the particle in an appropriate orientation for delivery of one or more encapsulated biologics. In cases where a biphasic particle has a tail extending from one portion of the particle surface, the tail can orient the particle within a blood vessel to direct the particle into a capillary. For example, a biphasic particle can be designed to have a tail to orient the particle within a blood vessel and direct the particle into a blood vessel (e.g., a capillary) where the encapsulated biologic can be delivered.

Biologics

Any appropriate biologic can be encapsulated within a particle described herein for delivery to a tissue. Examples of biologics that can be encapsulated within a particle described herein include, without limitation, nucleotides, polypeptides, small molecules, microvesicles, exosomes, extracellular vesicles, engineered cells, or combinations thereof. In some cases, a biologic can be a purified biologic (e.g., purified microvesicles or exosomes).

A particle (e.g., an alginate gel) described herein can be used to encapsulate one or more polypeptides. In some cases, a particle described herein can be used to encapsulate one or more polypeptides useful to treat a mammal experiencing a major adverse cardiac event (e.g., acute myocardial infarction) and/or a mammal at risk of experiencing a major adverse cardiac event (e.g., patients who underwent PCI for STEMI). For example, a particle encapsulating a biologic described herein can encapsulate one or more polypeptides useful for regenerating cardiac function and/or tissue or a nucleotide that encodes such a polypeptide. Examples of polypeptides useful for regenerating cardiac function and/or tissue include, without limitation, antibodies having the ability to neutralize tumor necrosis factor (TNF; e.g., TNF-α) activity, antibodies having the ability to neutralize mitochondrial complex-1 activity, and resolvin-D1 agonists.

Figure 15:
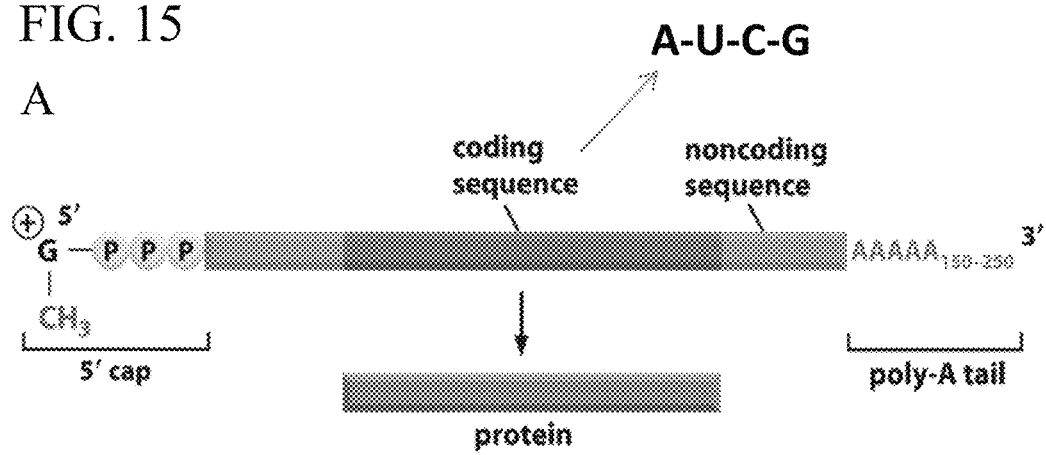
FIG. 15. Several RNA designs modifying the 5'CAP and the poly(A) tail for sustained gene expression in vivo without DNA integration. (A) Native mRNA. (B) Loop engineered modified mRNA adding a protective loop to the end of the poly(A) tail. (C) Loop poly(A) tail plus modification of the 5' 7-methyl guanosine cap to further limit degradation.
Figure 15:
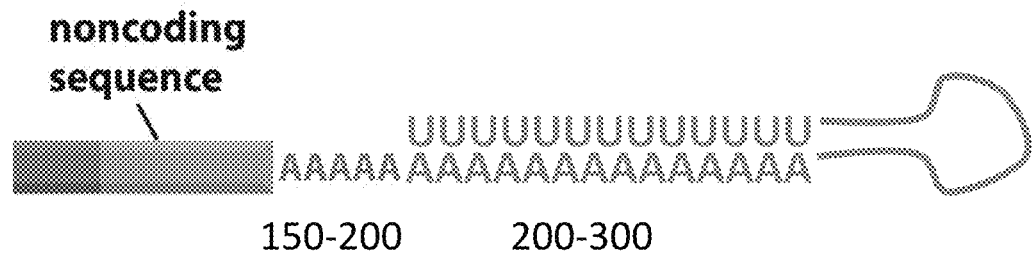
Figure 15:
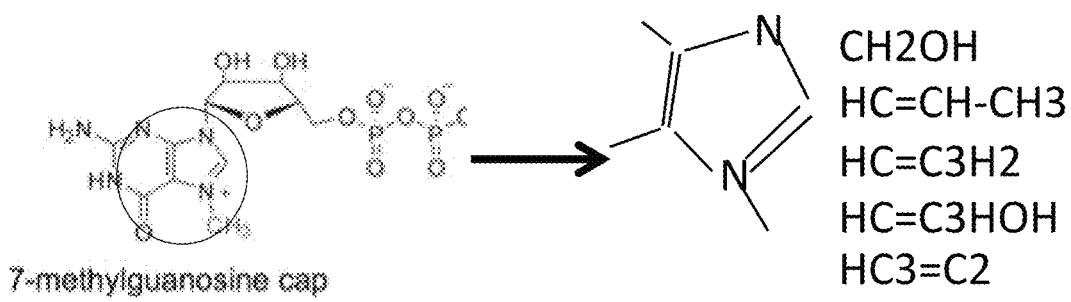

A particle (e.g., an alginate gel) described herein can be used to encapsulate one or more nucleotides. Examples of nucleotides that can be encapsulated within a particle include, without limitation, mRNAs, inhibitory RNAs (e.g., antisense RNAs, microRNAs (miRNAs), small interfering RNAs (siRNAs), short hairpin RNAs (shRNAs), and ago-miRs), antagomiRs, modified mRNAs, loop-engineered modified mRNAs (see, e.g., FIG. 15), or combinations thereof.

In some cases, a particle (e.g., an alginate gel) described herein can be used to encapsulate one or more mRNAs useful to treat a mammal experiencing a major adverse cardiac event (e.g., acute myocardial infarction) and/or a mammal at risk of experiencing a major adverse cardiac event (e.g., patients who underwent PCI for STEMI). For example, a particle encapsulating a biologic described herein can encapsulate one or more mRNAs encoding a polypeptide useful for regenerating cardiac function and/or tissue can be encapsulated within a particle described herein. Examples of polypeptides that can be useful for regenerating cardiac function and/or tissue include, without limitation, TNF-α, mitochondrial complex-1, resolvin-D1, NAP-2, TGF-α, ErBb3, VEGF, IGF-1, FGF-2, PDGF, IL-2, CD19, CD20, CD80/86, polypeptides described in WO 2015/034897, or an antibody directed against any of the foregoing polypeptides. For example, a human Nap-2 polypeptide can have the amino acid sequence set forth in, for example, National Center for Biotechnology Information (NCBI) Accession No. NP_002695.1 (GI No. 5473) and can be encoded by the nucleic acid sequence set forth in NCBI Accession No. NM_002704 (GI No. 5473). In some cases, a human TGF-α polypeptide can have the amino acid sequence set forth in NCBI Accession No. NP_003227.1 (GI No. 7039) and can be encoded by the nucleic acid sequence set forth in NCBI Accession No. NM_003236 (GI No. 7039). In some cases, a human ErBb3 polypeptide can have the amino acid sequence set forth in NCBI Accession No. NP_001005915.1 or NP_001973.2 (GI No. 2065) and can be encoded by the nucleic acid sequence set forth in NCBI Accession No. NM_001005915.1 or NM_001982.3 (GI No. 2065). For example, a human VEGF can have the amino acids set forth in NCBI Accession Nos. AAA35789.1 (GI: 181971), CAA44447.1 (GI: 37659), AAA36804.1 (GI: 340215), or AAK95847.1 (GI: 15422109), and can be encoded by the nucleic acid sequence set forth in NCBI Accession No. AH001553.1 (GI: 340214). For example, a human IGF-1 can have the amino acid sequence set forth in NCBI Accession No. CAA01954.1 (GI: 1247519) and can be encoded by the nucleic acid sequence set forth in NCBI Accession No. A29117.1 (GI: 1247518). For example, a human FGF-2 can have the amino acid sequence set forth in NCBI Accession No. NP_001997.5 (GI: 153285461) and can be encoded by the nucleic acid sequence set forth in NCBI Accession No. NM_002006.4 (GI: 153285460). For example, a human PDGF can have the amino acid sequence set forth in NCBI Accession No. AAA60552.1 (GI: 338209) and can be encoded by the nucleic acid sequence set forth in NCBI Accession No. AH002986.1 (GI: 338208). For example, a human IL-2 can have the amino acid sequence set forth in NCBI Accession No. AAB46883.1 (GI: 1836111) and can be encoded by the nucleic acid sequence set forth in NCBI Accession No. S77834.1 (GI: 999000). For example, a human CD19 can have the amino acid sequence set forth in NCBI Accession No. AAA69966.1 (GI: 901823) and can be encoded by the nucleic acid sequence set forth in NCBI Accession No. M84371.1 (GI: 901822). For example, a human CD20 can have the amino acid sequence set forth in NCBI Accession No. CBG76695.1 (GI: 285310157) and can be encoded by the nucleic acid sequence set forth in NCBI Accession No. AH003353.1 (GI: 1199857). For example, a human CD80 can have the amino acid sequence set forth in NCBI Accession No. NP_005182.1 (GI: 4885123) and can be encoded by the nucleic acid sequence set forth in NCBI Accession No. NM_005191.3 (GI: 113722122), and a human CD86 can have the amino acid sequence set forth in NCBI Accession No. AAB03814.1 (GI: 439839) and can be encoded by the nucleic acid sequence set forth in NCBI Accession No. CR541844.1 (GI: 49456642). For example, a polypeptide that can be useful for regenerating cardiac function and/or tissue can be an antibody directed against TNF-α, mitochondrial complex-1, or resolvin-D1. In some cases, a particle encapsulating a biologic described herein can encapsulate one or more mRNAs encoding NAP-2 and/or TGF-α.

In some cases, a particle (e.g., an alginate gel) described herein can be used to encapsulate one or more inhibitory RNAs useful to treat a mammal experiencing a major adverse cardiac event (e.g., acute myocardial infarction) and/or a mammal at risk of experiencing a major adverse cardiac event (e.g., patients who underwent PCI for STEMI). For example, a particle described herein can encapsulate one or more inhibitory RNAs inhibiting and/or reducing expression of one or more of the following polypeptides: eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, MMP-3, and polypeptides described in WO 2015/034897. For example, a human eotaxin-3 polypeptide can have an amino acid sequence set forth in, for example, NCBI Accession No: No. NP_006063.1 (GI No. 10344) and can be encoded by the nucleic acid sequence set forth in NCBI Accession No. NM_006072 (GI No. 10344). In some cases, a human cathepsin-S can have the amino acid sequence set forth in NCBI Accession No. NP_004070.3 (GI No. 1520) and can be encoded by the nucleic acid sequence set forth in NCBI Accession No. NM_004079.4 (GI No. 1520). In some cases, a human DK-1 can have the amino acid sequence set forth in NCBI Accession No. NP_036374.1 (GI No. 22943) and can be encoded by the nucleic acid sequence set forth in NCBI Accession No. NM_012242 (GI No. 22943). In some cases, a human follistatin can have then amino acid sequence set forth in NCBI Accession No. NP_037541.1 (GI No. 10468) and can be encoded by the nucleic acid sequence set forth in NCBI Accession No. NM_013409.2 (GI No. 10468). In some cases, a human ST-2 can have the amino acid sequence set forth in NCBI Accession No. BAA02233 (GI No. 6761) and can be encoded by the nucleic acid sequence set forth in NCBI Accession No D12763.1 (GI No 6761). In some cases, a human GRO-α polypeptide can have the amino acid sequence set forth in NCBI Accession No. NP_001502.1 (GI No. 2919) and can be encoded by the nucleic acid sequence set forth in NCBI Accession No. NM_001511 (GI No. 2919). In some cases, a human IL-21 can have the amino acid sequence set forth in NCBI Accession No. NP_068575.1 (GI No. 59067) and can be encoded by the nucleic acid sequence set forth in NCBI Accession No. NM_021803 (GI No. 59067). In some cases, a human NOV polypeptide can have the amino acid sequence set forth in NCBI Accession No. NP_002505.1 (GI No. 4856) and can be encoded by the nucleic acid sequence set forth in NCBI Accession No. NM_002514 (GI No. 4856). In some cases, a human transferrin polypeptide can have the amino acid sequence set forth in NCBI Accession No. NP_001054.1 (GI No. 7018) and can be encoded by the nucleic acid sequence set forth in NCBI Accession No. NM_001063.3 (GI No. 7018). In some cases, a human TIMP-2 polypeptide can have the amino acid sequence set forth in NCBI Accession No. NP_003246.1 (GI No. 7077) and can be encoded by the nucleic acid sequence set forth in NCBI Accession No. NM_003255.4 (GI No. 7077). In some cases, a human TNFαRI polypeptide can have the amino acid sequence set forth in NCBI Accession No. NP_001056.1 (GI No. 7132) and can be encoded by the nucleic acid sequence set forth in NCBI Accession No. NM_001065 (GI No. 7132). In some cases, a human TNFαRII polypeptide can have the amino acid sequence set forth in NCBI Accession No. NP_001057.1 (GI No. 7133) and can be encoded by the nucleic acid sequence set forth in NCBI Accession No. NM_001066 (GI No. 7133). In some cases, a human angiostatin polypeptide can have the amino acid sequence set forth in NCBI Accession No. NP_000292 (GI No. 5340) and can be encoded by the nucleic acid sequence set forth in NCBI Accession No. NM_000301 (GI No. 5340). In some cases, a human CCL25 polypeptide can have the amino acid sequence set forth in NCBI Accession No. NP_005615.2 (GI No. 6370) and can be encoded by the nucleic acid sequence set forth in NCBI Accession No. NM_005624 (GI No. 6370). In some cases, a human ANGPTL4 polypeptide can have the amino acid sequence set forth in NCBI Accession No. NP_001034756.1 or NP_647475.1 (GI No. 51129) and can be encoded by the nucleic acid sequence set forth in NCBI Accession No. NM_001039667.1 or NM_139314.1 (GI No. 51129). In some cases, a human MMP-3 polypeptide can have the amino acid sequence set forth in NCBI Accession No. NP_002413.1 (GI No. 4314) and can be encoded by the nucleic acid sequence set forth in NCBI Accession No. NM_002422 (GI No. 4314).

In some cases, a particle (e.g., an alginate gel) described herein can be used to encapsulate one or more nucleotides that modulate (e.g., mimic or inhibit) microRNAs involved in cardiac regenerative potency. For example, a particle described herein can be used to encapsulate one or more agomiRs that mimic one or more miRNAs to augment cardiac regenerative potency. For example, a particle described herein can be used to encapsulate one or more antagomiRs that inhibit one or more miRNAs to augment cardiac regenerative potency. Examples of miRNAs involved in cardiac regenerative potency include, without limitation, miR-127, miR-708, miR-22-3p, miR-411, miR-27a, miR-29a, miR-148a, miR-199a, miR-143, miR-21, miR-23a-5p, miR-23a, miR-146b-5p, miR-146b, miR-146b-3p, miR-2682-3p, miR-2682, miR-4443, miR-4443, miR-4521, miR-4521, miR-2682-5p, miR-2682, miR-137. miR-137, miR-549. miR-549, miR-335-3p, miR-335, miR-181c-5p, miR-181c, miR-224-5p, miR-224, miR-3928, miR-3928, miR-324-5p, miR-324, miR-548h-5p, miR-548h-1, miR-548h-5p, miR-548h-2, miR-548h-5p, miR-548h-3, miR-548h-5p, miR-548h-4, miR-548h-5p, miR-548h-5, miR-4725-3p, miR-4725, miR-92a-3p, miR-92a-1, miR-92a-3p, miR-92a-2, miR-134, miR-134, miR-432-5p, miR-432, miR-651, miR-651, miR-181a-5p, miR-181a-1, miR-181a-5p, miR-181a-2, miR-27a-5p, miR-27a, miR-3940-3p, miR-3940, miR-3129-3p, miR-3129, miR-146b-3p, miR-146b, miR-940, miR-940, miR-484, miR-484, miR-193b-3p, miR-193b, miR-651, miR-651, miR-15b-3p, miR-15b, miR-576-5p, miR-576, miR-377-5p, miR-377, miR-1306-5p, miR-1306, miR-138-5p, miR-138-1, miR-337-5p, miR-337, miR-135b-5p, miR-135b, miR-16-2-3p, miR-16-2, miR-376c. miR-376c, miR-136-5p, miR-136, let-7b-5p, let-7b, miR-377-3p, miR-377, miR-1273g-3p, miR-1273g, miR-34c-3p, miR-34c, miR-485-5p, miR-485, miR-370. miR-370, let-7f-1-3p, let-7f-1, miR-3679-5p, miR-3679, miR-20a-5p, miR-20a, miR-585. miR-585, miR-3934, miR-3934, miR-127-3p, miR-127, miR-424-3p, miR-424, miR-24-2-5p, miR-24-2, miR-130b-5p, miR-130b, miR-138-5p, miR-138-2, miR-769-3p, miR-769, miR-1306-3p, miR-1306, miR-625-3p, miR-625, miR-193a-3p, miR-193a, miR-664-5p, miR-664, miR-5096. miR-5096, let-7a-3p, let-7a-1, let-7a-3p, let-7a-3, miR-15b-5p, miR-15b, miR-18a-5p, miR-18a, let-7e-3p, let-7e, miR-1287. miR-1287, miR-181c-3p, miR-181c, miR-3653, miR-3653, miR-15b-5p, miR-15b, miR-1, miR-1-1, miR-106a-5p, miR-106a, miR-3909. miR-3909, miR-1294. miR-1294, miR-1278, miR-1278, miR-629-3p, miR-629, miR-340-3p, miR-340, miR-200c-3p, miR-200c, miR-22-3p, miR-22, miR-128, miR-128-2, miR-382-5p, miR-382, miR-671-5p, miR-671, miR-27b-5p, miR-27b, miR-335-5p, miR-335, miR-26a-2-3p, miR-26a-2, miR-376b. miR-376b, miR-378a-5p, miR-378a, miR-1255a, miR-1255a, miR-491-5p, miR-491, miR-590-3p, miR-590, miR-32-3p, miR-32, miR-766-3p, miR-766, miR-30c-2-3p, miR-30c-2, miR-128. miR-128-1, miR-365b-5p, miR-365b, miR-132-5p, miR-132, miR-151b. miR-151b, miR-654-5p, miR-654, miR-374b-5p, miR-374b, miR-376a-3p, miR-376a-1, miR-376a-3p, miR-376a-2, miR-149-5p, miR-149, miR-4792. miR-4792, miR-1. miR-1-2, miR-195-3p, miR-195, miR-23b-3p, miR-23b, miR-127-5p, miR-127, miR-574-5p, miR-574, miR-454-3p, miR-454, miR-146a-5p, miR-146a, miR-7-1-3p, miR-7-1, miR-326. miR-326, miR-301a-5p, miR-301a, miR-3173-5p, miR-3173, miR-450a-5p, miR-450a-1, miR-7-5p, miR-7-1, miR-7-5p, miR-7-3, miR-450a-5p, miR-450a-2, miR-1291, miR-1291, miR-7-5p, miR-7-2, and miR-17-5p, miR-17.

Nucleotides (e.g., RNA) encapsulated within a particle described herein can be modified nucleotides. In some cases, nucleotides can be modified for increased stability. For example, one or more uracil residues of an RNA described herein can be replace with a modified uracil residue. Examples of modified uracil residues include, without limitation, pseudouridine (Ψ), dihydrouridine (D), and dideoxyuracil. An mRNA may be modified to form a biofunctionalized microencapsulated modified mRNA (M³RNA), which are described in more detail below.

A particle (e.g., an alginate gel) described herein can be used to encapsulate other molecules in addition to or in place of a biologic. In some cases, a particle (e.g., an alginate gel) described herein can be used to encapsulate one or more small molecules. For example, a particle described herein can be used to encapsulate one or more small molecules useful to treat a mammal experiencing a major adverse cardiac event (e.g., acute myocardial infarction) and/or a mammal at risk of experiencing a major adverse cardiac event (e.g., patients who underwent PCI for STEMI). For example, a particle described herein can encapsulate one or more small molecules useful for regenerating cardiac function and/or tissue. Examples of small molecules useful for regenerating cardiac function and/or tissue include, without limitation, lipopolysaccharides, tumor necrosis factor (e.g., TNF-α) antagonists, mitochondrial complex-1 antagonists, and resolvin-D1 agonists. In some cases, a particle (e.g., an alginate gel) described herein can be used to encapsulate one or more microvesicles and/or exosomes. In some cases, a particle described herein can be used to encapsulate one or more microvesicles and/or exosomes useful to treat a mammal experiencing a major adverse cardiac event (e.g., acute myocardial infarction) and/or a mammal at risk of experiencing a major adverse cardiac event (e.g., patients who underwent PCI for STEMI). For example, a particle described herein can encapsulate one or more microvesicles and/or exosomes useful for regenerating cardiac function and/or tissue. Examples of microvesicles and exosomes useful for regenerating cardiac function and/or tissue include, without limitation, microvesicles and exosomes isolated from plasma, blood-derived products, and cultured stem cells.

A particle (e.g., an alginate gel) described herein also can include one or more detectable labels. A detectable label can be incorporated into the particle or encapsulated within the particle. Examples of detectable molecules include, without limitation, bioluminescent label (e.g., luciferase), fluorescent molecules (e.g., GFP and mCherry), and radionuclide molecules. In some cases, an mRNA expressing a detectable label is encapsulated within a particle such that temporal and/or spatial delivery of the encapsulated RNA can be monitored in a mammal.

A particle (e.g., an alginate gel) described herein also can include one or more additional therapeutic molecules. A therapeutic molecule can be conjugated to a particle, embedded within a particle, encapsulated within a particle, or any combination thereof. Examples of therapeutic agents include, without limitation, stem cells (e.g., mesenchymal stem cells, cardiac stem cells, and bone marrow), pharmaceuticals (e.g., statins, analgesics, chemotherapeutics, beta blockers, antibiotics, and nutrients (e.g., carbohydrates, fats, vitamins, and minerals).

In some cases, a particle (e.g., an alginate gel) encapsulating one or more biologics described herein can be used to encapsulate one or more nucleotides useful for treating other diseases and/or conditions.

Microencapsulated Modified mRNA (M³RNA)

M³RNA is a unique platform by which to induce rapid expression of encoded genes into a broad array of tissues. In the context of the M³RNA platform, M³RNA refers to modified microencapsulated mRNA; naked modified RNA (unencapsulated) is referred to as M²RNA. M³RNA is well suited for generating antibodies against new infectious threats. Intrinsic to this technological platform is the ability to rapidly scale within a short timeframe and simultaneously deliver multiple gene constructs. Due to the use of mRNA as the driving biologics within this platform, there is no integrative or mutation risk with therapy. Furthermore, unlike AAV and other viral gene-delivery technologies, the M³RNA platform avoids risk of immune reaction to the delivery system allowing its repetitive use with different constructs. M³RNA can be readily evolved into an M³RNA-Ig delivery system allowing efficient, rapid and sustained expression of antibodies against putative pathogens following delivery.

M³RNA has been tested to deliver several reporter and therapeutic gene constructs in both in vitro and in vivo models. Further, M³RNA can accommodate multi-gene therapeutic capability. M³RNA can simultaneously deliver, for example, several cardioregenerative genes in the setting of acute myocardial infarction. Specific to the transformation of M³RNA towards an M³RNA-Ig platform, is the demonstration of simultaneous delivery of reporter genes that emulate the size of IgG heavy and light chains in the form of GFP/mCherry mRNA (720 bp) and Firefly Luciferase (FLuc) mRNA (1653 bp). The system has been scaled to a three-gene delivery platform in vivo demonstrating similar penetrance for all reporter genes tested. The microencapsulated modified messenger RNA achieves rapid and robust protein expression within multiple cell lines and primary cells (human dermal fibroblasts, human cardiac fibroblasts, HEK293 cells, HL-1 cardiomyocytes, HUVAC cells, neonatal rat cardiomyocytes, and neonatal rat skeletal muscle cells). Furthermore, microencapsulating M³RNA using, for example, PEGylated charged nanoparticles induce rapid (within two hours) in vivo expression following direct injection into multiple organ systems (including both skeletal and cardiac muscle) in murine and porcine models.

Figure 16:
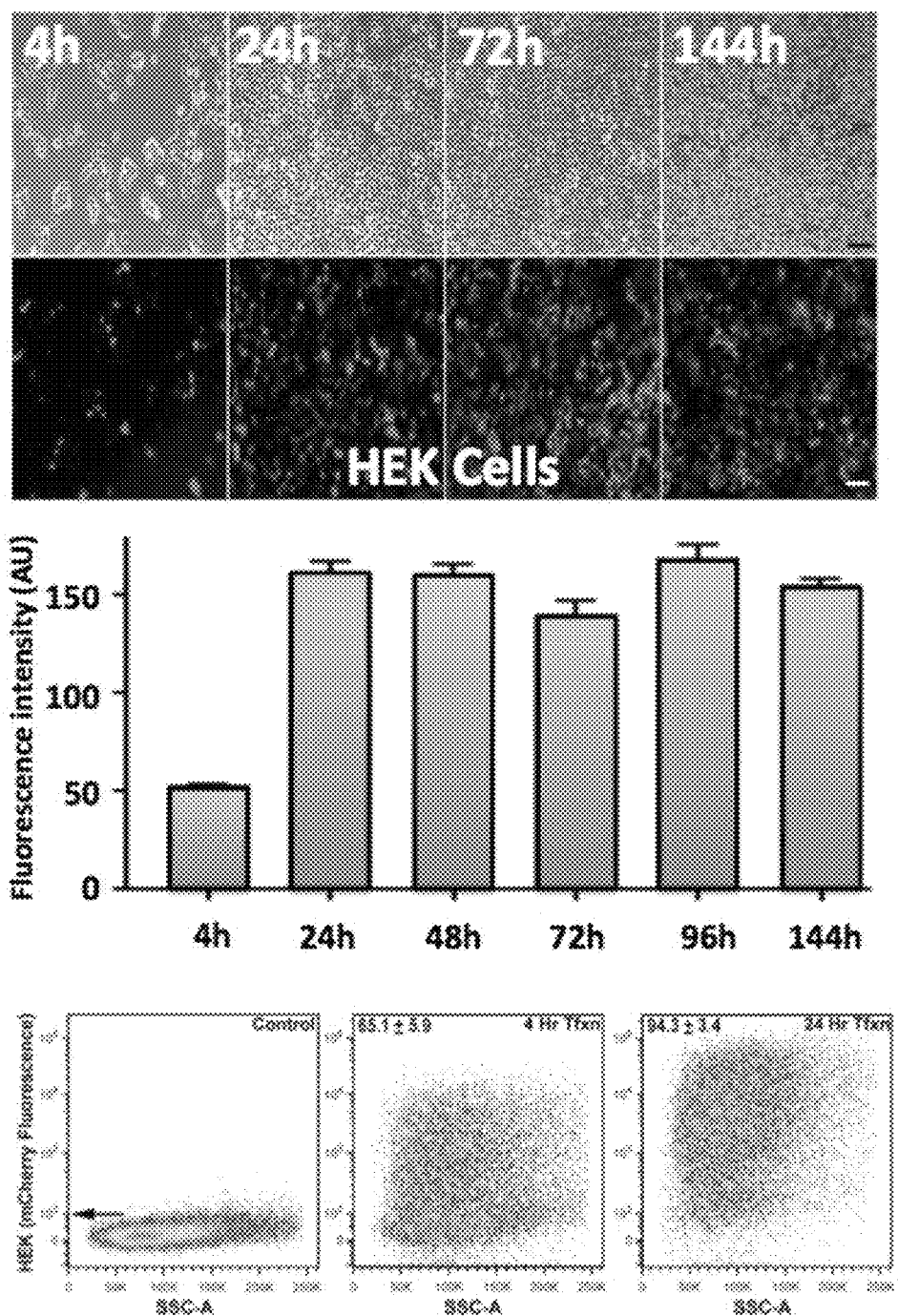
FIG. 16. Transfection of HEK cells will M$^2$RNA encoding mCherry results in rapid gene induction that is sustained for a six-day observation period.

Kinetics of M²RNA (modified mCherry mRNA) transfected into HEK293 (human embryonic kidney) cells resulted in mCherry protein expression in as early as two hours. Daily quantification of expression yielded fluorescence images for HEK293 cells at indicated time periods are shown in FIG. 16 showing a rapid, robust, and sustained protein expression upon mRNA transfection for up to six days. Quantification of fluorescence intensity within these cells (>10 fields of cells/time period) documented increasing fluorescence intensity in the initial 24 hours, sustained up to six days. Using flow cytometry as the gold standard for quantitation of transfection efficiency, analysis of mCherry protein expression levels at four hours and 24 hours post-transfection was performed. Scatter plots, with the fluorescence intensity on the x-axis and sideward scattering signal on the y-axis, revealed the consistent bimodal population upon transfection (FIG. 16) with the transition revealing the number of transfected cells as seen at four hours and 24 hours documenting a transfection efficiency of approximately 95%.

Figure 17:
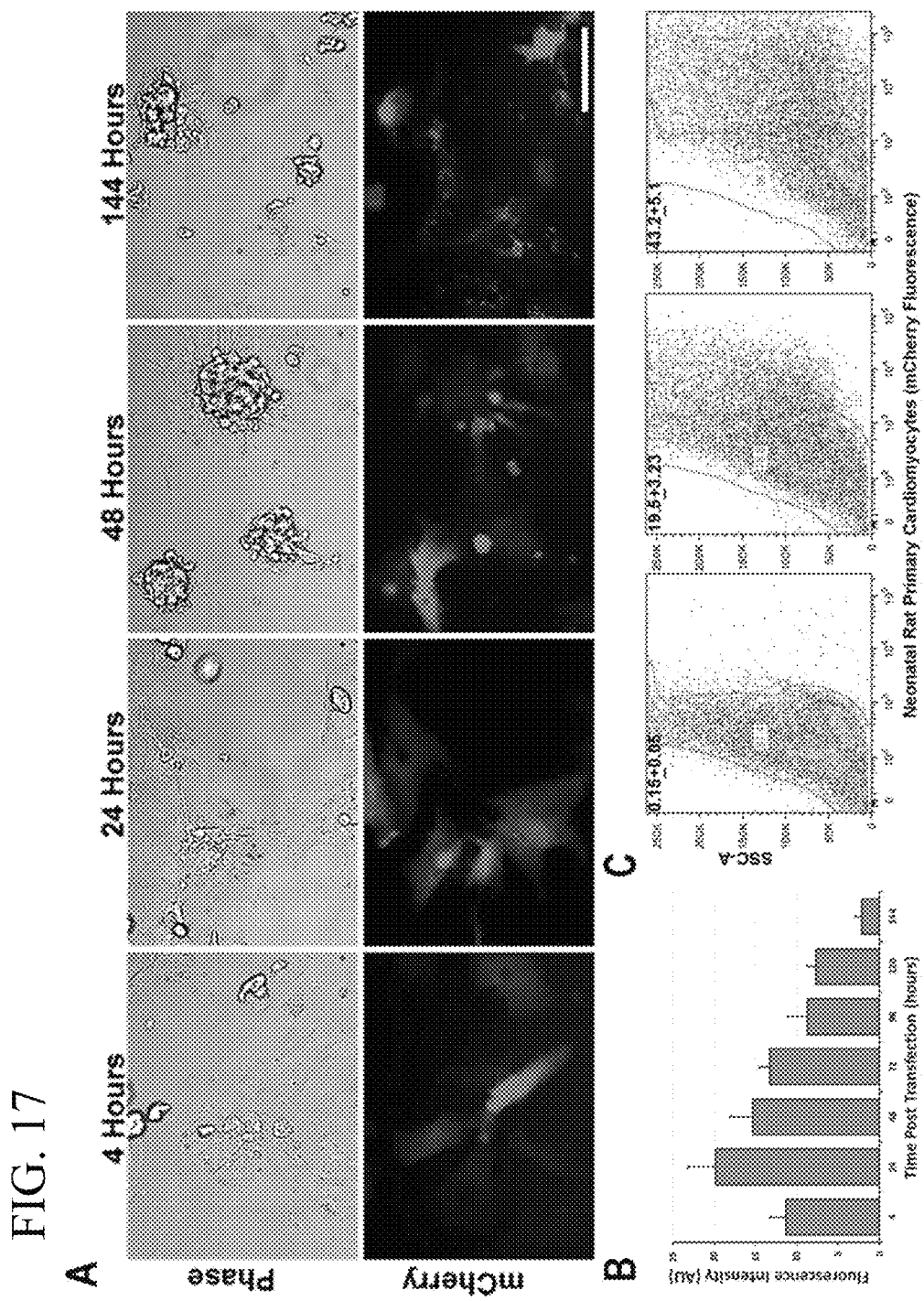
FIG. 17. Data showing persistent expression of M$^3$RNA. (A) M$^3$RNA induces mCherry in primary cultured cardiomyocytes. Temporal visualization of mCherry expression over a six-day observation period indicates persistence of quantified expression. (C) Flow cytometric evaluation reveals 43% efficiency in inducing cultured cardiomyocytes.

The M³RNA platform is compatible with "hard-to-transfect" primary cell phenotypes such as, for example, neonatal rat cardiomyocytes. Neonatal primary cardiomyocytes were isolated and plated yielding synchronous beating pattern of cardiomyocytes in the dishes. Cardiomyocytes were transfected with mCherry M³RNA and fluorescence images were acquired starting at four hours post-transfection for six days. Representative images for multiple time periods are shown in FIG. 17A, indicating rapid, robust, and sustained protein expression within primary cardiomyocytes. Quantification of the fluorescence intensity within these primary cardiomyocytes revealed that maximum expression occurred at 24 hours and was sustained, but declining, for up to six days (FIG. 17B). Transfection efficiency within these primary cardiomyocytes was furthermore assessed using flow cytometry at four hours and 24 hours by transfecting the cells with mCherry mRNA with scatter plot analysis demonstrating a transfection efficiency of 43% at 24 hours (FIG. 17C). Transfection of primary cardiomyocytes the M³RNA platform did not alter the structural or functional characteristics of cardiomyocytes.

Figure 18:
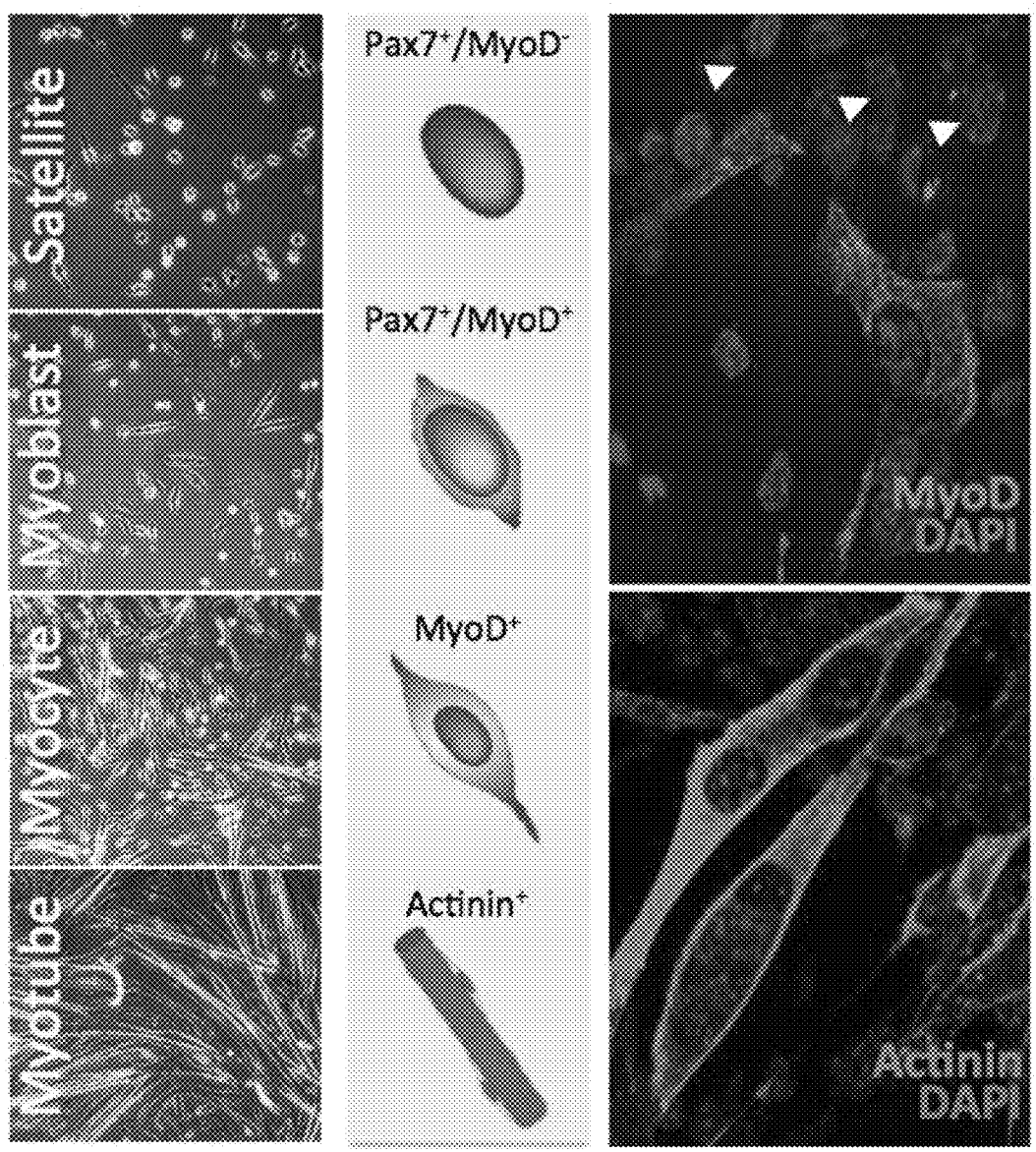
FIG. 18. Primary human skeletal muscle culture system. Derived from donor samples, master cell bank of P3 myoblasts are generated within a defined xeno-free propagation medium. Within a differentiation environment MyoD$^+$ cells can be induced to differentiate into actinin-positive myotubes.
Figure 19:
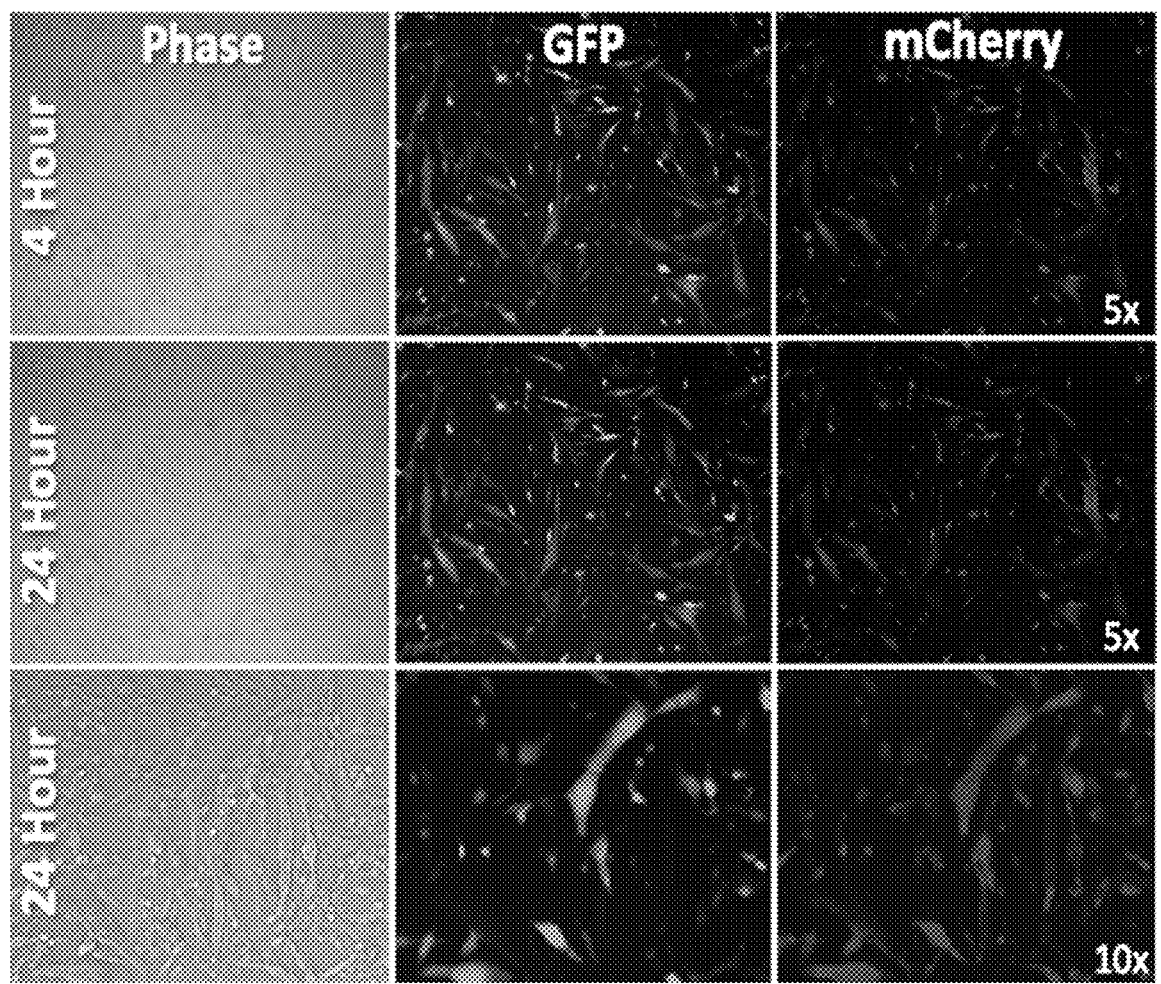
FIG. 19. M$^3$RNA-mediated dual gene expression within a single encapsulation system. Induction of both GFP and mCherry within four hours and persistent expression over a 24-hour observation period within primary cultures skeletal muscle cells.

The M³RNA platform also is compatible with intramuscular delivery, providing high transfection efficiency comparable with results obtained with primary cardiomyocyte cultures (FIG. 19). The data presented in FIG. 19 employ a primary human skeletal muscle culture system that involves large-scale isolation of satellite cells from surgically disposed human skeletal muscle tissue. Within a defined xeno-free cultivating culture condition, skeletal muscle donor tissue is used to derive skeletal muscle satellite progenitor populations. Cells undergo mycoplasma/sterility profiling over a three-week culture period and are cryopreserved. Prior to derivation of master cell banks, each lot of cryopreserved satellite cells undergoes quality assurance evaluation testing myogenic potency via immunohistochemistry (FIG. 18), gene expression profiling and automated microscopic visualization of myotube formation (FIG. 18). With confirmation of potency and sterility, each lot is expanded in three passages (P3) to generate a master cell bank of 200 million cells frozen as 1 million cell aliquots. Master cell bank lots are subjected to repeat quality assurance and sterility assessment prior to experimental use. P3 cells can be induced to generate primary human skeletal muscle cells within 2-3 days through culture within a defined medium (FIG. 18).

Figure 20:
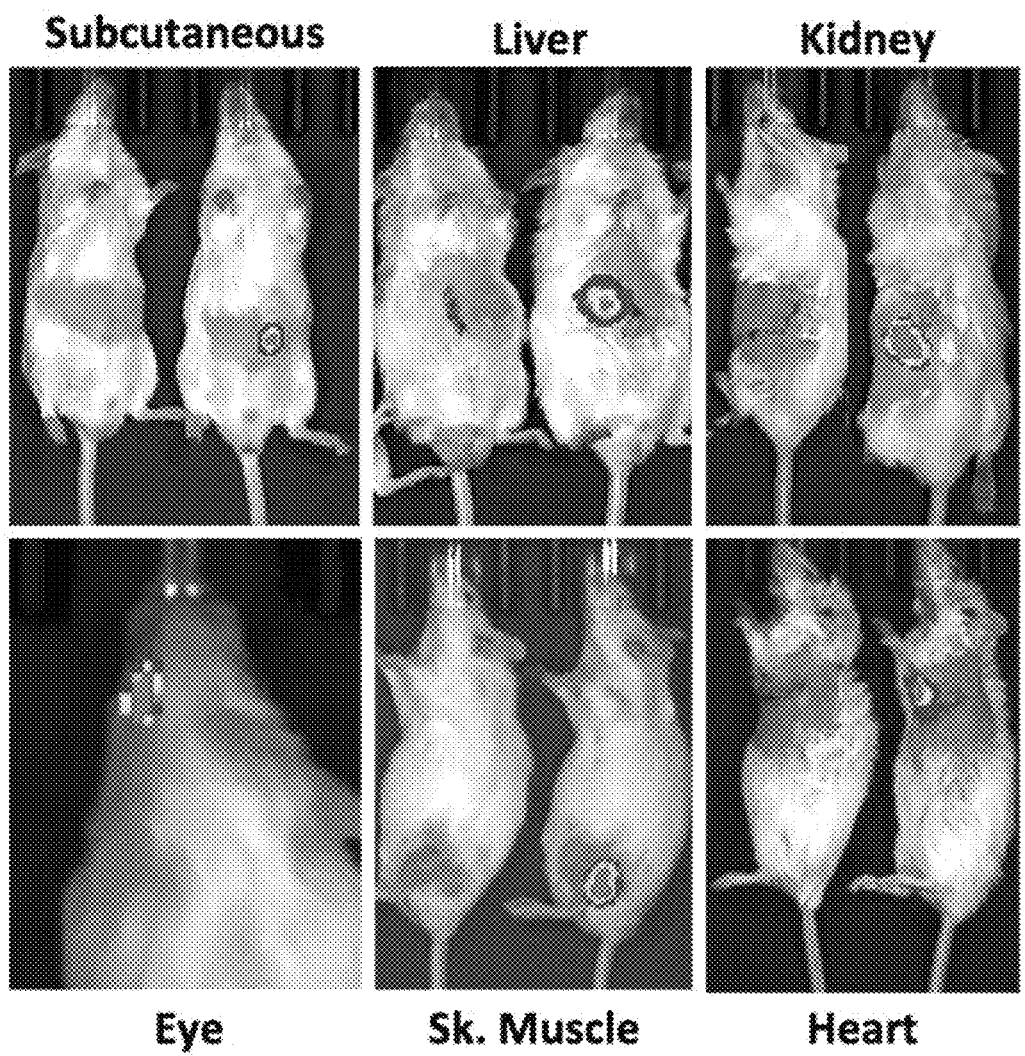
FIG. 20. In vivo delivery of Fluc M$^3$RNA demonstrates compatibility of this platform in a broad array of tissues. Sham controls are provided for each example with the exception of the eye, where the contralateral eye served as sham control.

Microencapsulation of modified messenger RNA within a PEGylated cation-based micro particle system provides an exemplary platform by which to deliver M³RNA in vivo. Reporter genes including mCherry (720 bp), GFP (720 bp) mRNA, and Firefly Luciferase (FLuc) mRNA (1653 bp) were used in the in vivo setting. FLuc provided an added dimension to the analysis as the kinetics of protein expression in live animals could be prospectively documented. Using Luciferin to excite transfection areas provided an exact approach to decipher the localization of the M³RNA signal following delivery. Following optimization using a subcutaneous route, the M³RNA platform was tested in a broad array of tissues including intrahepatic, intrarenal, intraocular, intramuscular and intramyocardial delivery (FIG. 20). In every instance, FLuc expression could be demonstrated within the injected area within two hours following delivery and sustained for more than 72 hours.

Figure 21:
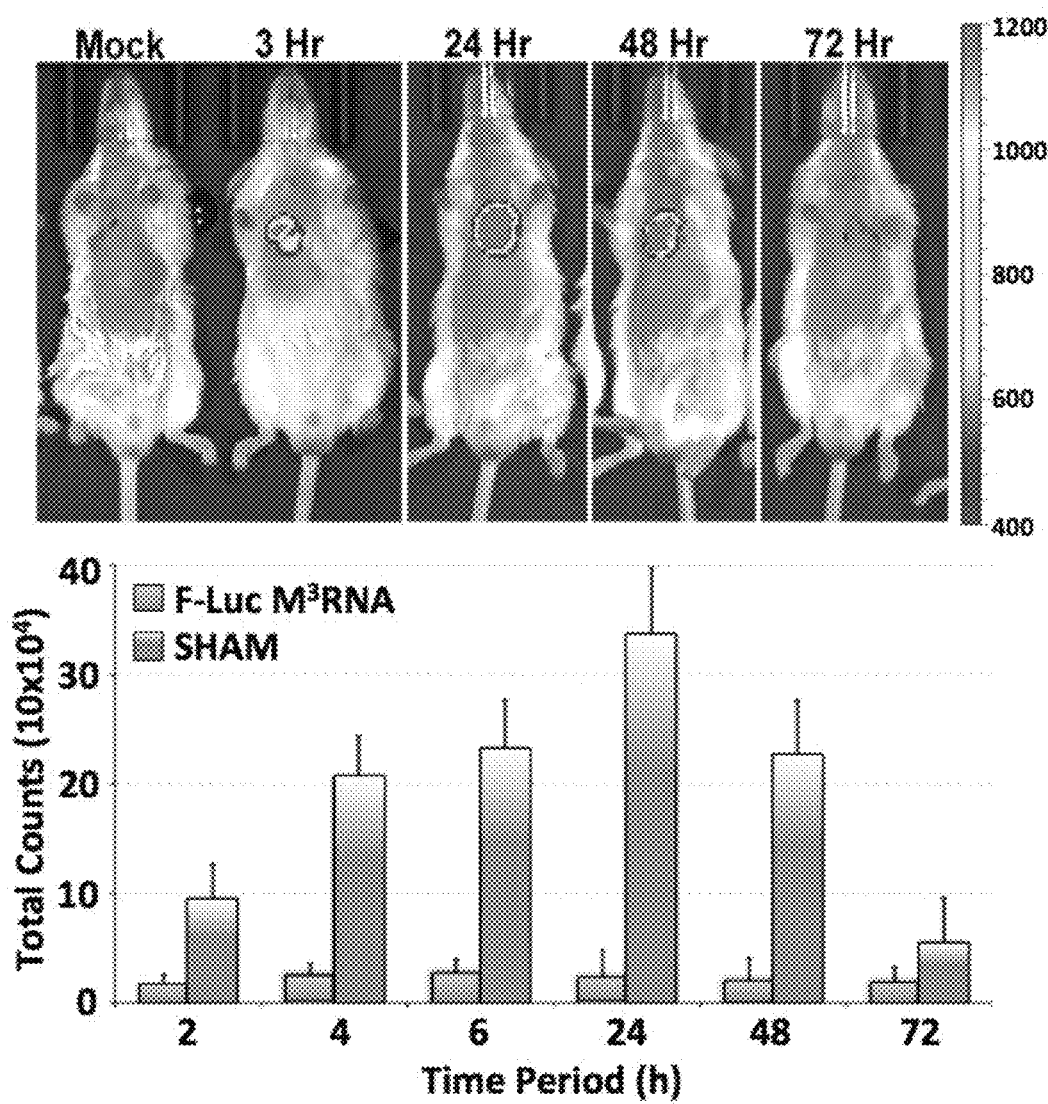
FIG. 21. Quantification of Fluc expression following delivery of M$^3$RNA via direct myocardial injection over a 72-hour observation period.
Figure 22:
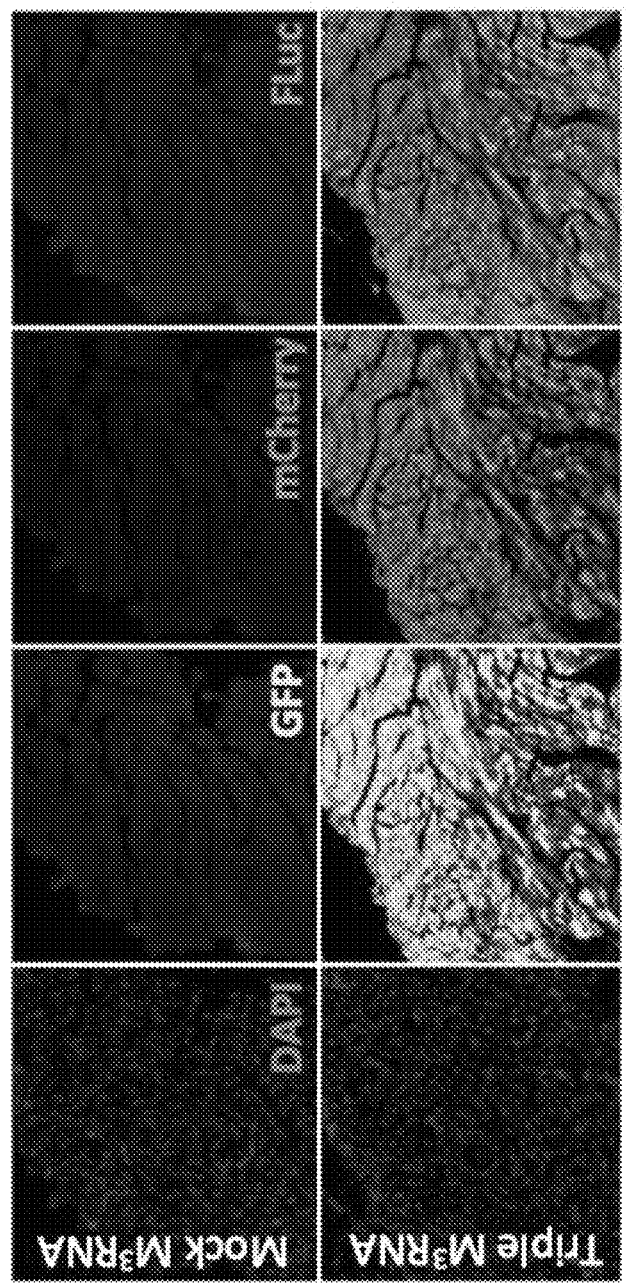
FIG. 22. Evidence for simultaneous delivery of three genes using the M$^3$RNA platform with direct myocardial injection.

Within the heart, rapid FLuc expression following direct myocardial injections of FLuc M³RNA into the anterior left ventricle was quantified at different time points, revealing rapid induction of gene expression sustained over a three-day observation period (FIG. 21). To demonstrate as a proof-of-concept that multiple gene induction is feasible, three different model constructs (mCherry, GFP, and FLuc) were simultaneously microencapsulated and delivered using a single myocardial injection in mice versus scrambled mock M³RNA controls. FLuc expression was confirmed at 24 hours within the heart using the bioluminescence assay in IVIS spectrum in vivo imaging system (FIG. 20, heart). Mice were then sacrificed and the heart was excised to assess expression by immunohistochemistry in histological sections confirming overlapping GFP, mCherry, and FLuc protein expression within the combined gene-M³RNA injected mice (lower panels) when compared to mock M³RNA mice (upper panels) (FIG. 22).

The M³RNA technology can be evolved to achieve a delivery platform for rapid creation of highly potent therapeutics. For example, biofunctionalized M³RNA can form the foundation of an M³RNA-Ig Delivery System (MIDS) capable of rapidly integrating new genetic sequences to target novel pathogens (e.g., viral pathogen such as, for example, Zika virus and H7N9).

Compatibility of the M³RNA platform for the gene length of IgG heavy and light chain has been confirmed with the concomitant use of FLuc and fluorescent reporter gene, showing simultaneous induction of up to three genes within cardiac muscle tissue in vivo. Rapid and sustainable expression of genes encoded in the M³RNA-Ig vector can be enhanced using specialized design of the 5' and 3' UTR of the RNA molecule. Design of the M³RNA-Ig vector can involve consideration of one or more of the following: (1) whether to join the heavy and light chain genes on a single transcript with a P2A ribosomal skipping sequence versus synthesis as separate transcripts; (2) the length/introduction of the 3'poly(A) tail; (3) the type of 5'm7G cap; (4) selection of modified nucleotides; (5) IRES and pseudoknot modification of the 5' and 3' UTR, respectively, to diminish rate of degradation; and/or (6) nanoparticle-mediated microencapsulation to identify an appropriate stoichiometry for in vivo skeletal muscle delivery.

Figure 23:
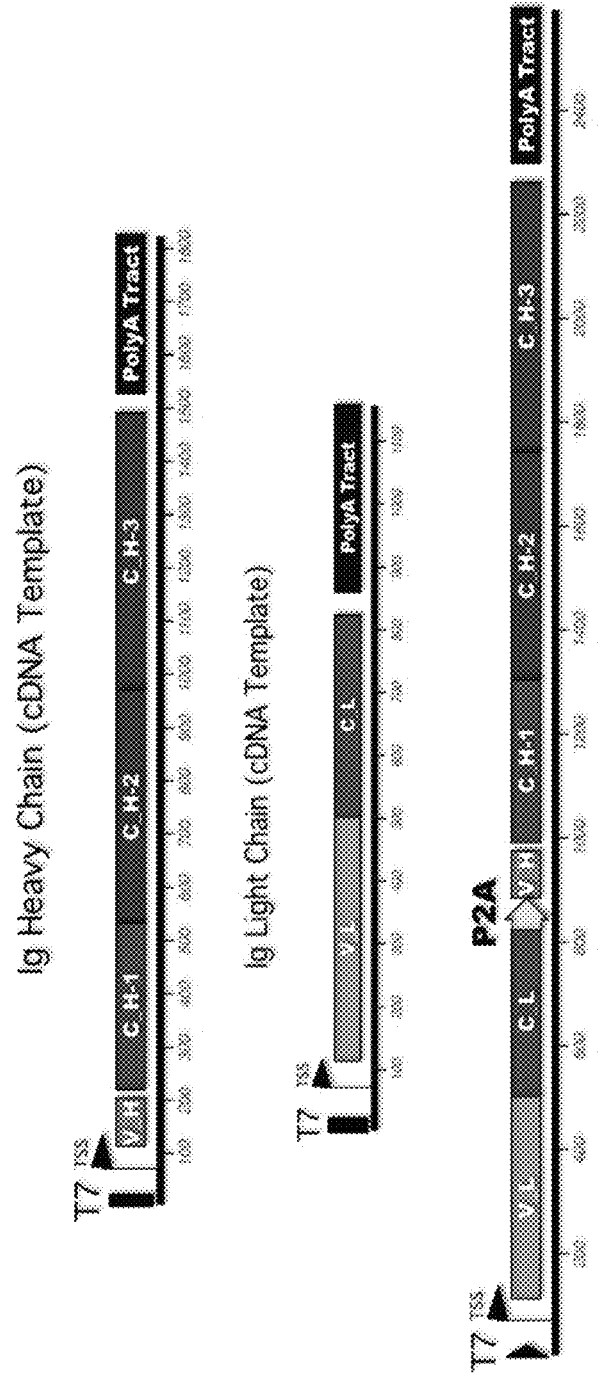
FIG. 23. Vector design strategy for establishment of the M$^3$RNA-Ig platform.

In some embodiments, the heavy and light chains can be synthesized on two separate transcripts. This approach allows rapid parallel work to incorporate the VL/VH antigen binding domains within a multicloning site (FIG. 23). Specifically, using two transcripts instead of one allows the separate DNA templates to be cloned at the same time instead of sequentially, thereby speeding development of new embodiments. Of course, where desired, one can design the vector so that the heavy chain and light chain are synthesized from a single transcript. mRNAs synthesized with poly(A) tail of 300 or more nucleotides have significant longer half-life and superior translational properties. In some embodiments, therefore, the vector can include a suitable promoter (e.g., T7), the heavy chain and light chain coding regions, and 300 nucleotide poly(T) tract will serve as the backbone template for mRNA transcription. Vectors can be designed as two separate versions to accommodate large variances in the C-regions of new antibodies identified. The initial design can assume an unchanging C-region in prospective antibodies identified. Accordingly, the multicloning site in the heavy chain and light chain vectors can allow rapid parallel introduction of the V sequence into this region and initiation of the M³RNA-Ig manufacturing process. Conversely, in certain cases, a varied Ig backbone may suggest adjustment also to the C regions of the parallel vector systems. As such, to ensure the capability for rapid response, additional vectors engineered with multi-cloning sites allowing for insertion of the entirety of the heavy and light chains can be designed.

Figure 24:
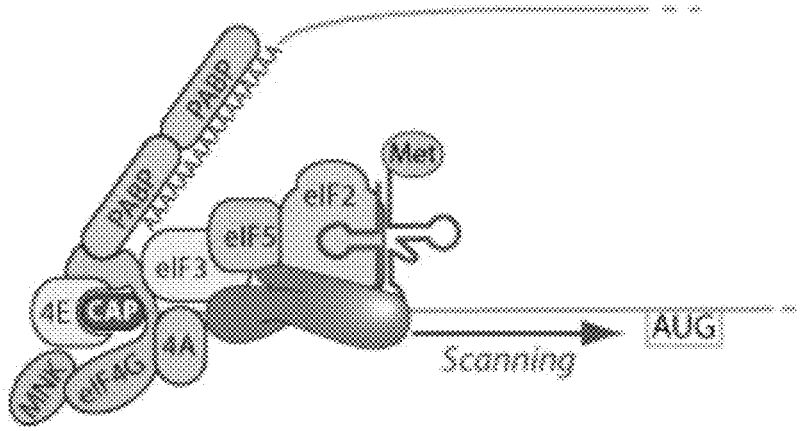
FIG. 24. Use of IRES sequence eliminates the need for a CAP/PABP dependent system.
Figure 24:
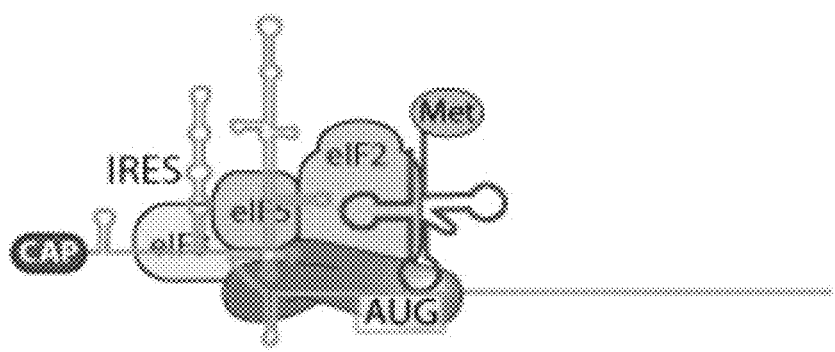

The mRNA CAP mediates efficiency of the expression of the gene product. In some embodiments, $M^3RNA$-Ig may be generated using CAP-1 as an approach to avoid any innate immune responses that may be mediated using CAP-0. A design including CAP-1 can include post-transcriptional modifications using a Vaccinia Capping System followed by a CAP 2' O-Methyltransferase. However, a CAP-dependent approach can involve interaction of the poly(A) binding protein (PABP), which can add significant length to the construct and thereby limit creativity at the 3' site to further limit RNA degradation (FIG. 24, top). Thus, in some embodiments, the $M^3RNA$-Ig system can include an integral ribosomal entry site (IRES) within the 5'UTR, eliminating the need for PABP interaction (FIG. 24, bottom).

An $M^3RNA$ system can limit undesirable side effects of mRNA transfection and/or slow degradation of the $M^3RNA$ by introducing modified nucleotides such as, for example, 5'-methylcytidine in place of cytosine or pseudouridine ($\Psi$), dihydrouridine (D), or dideoxyuracil in place of uracil. Modified NTPs are readily abundant as GMP starting material and can be rapidly introduced using standard RNA synthesis techniques, providing significant molecular and translational advantage following delivery.

Figure 25:
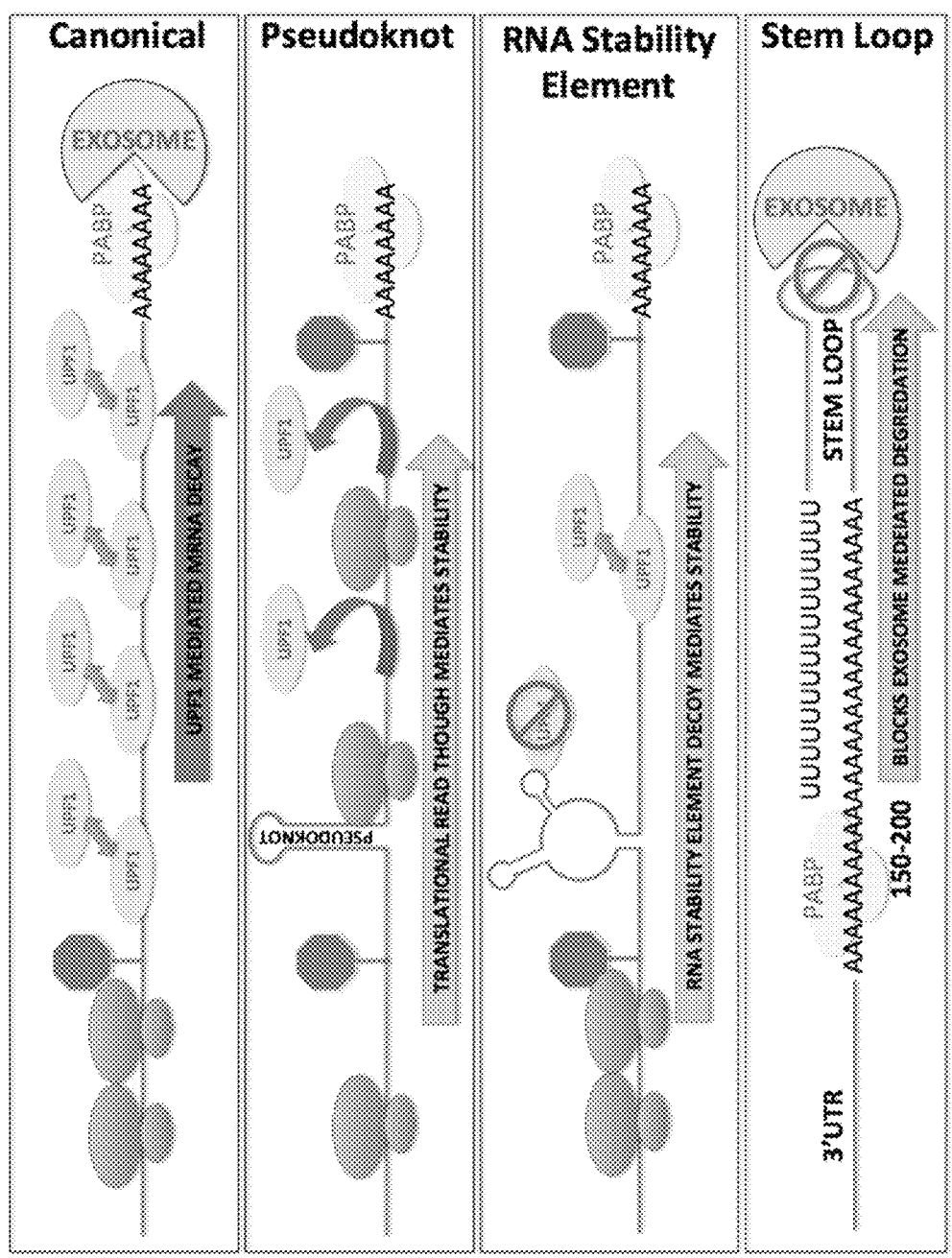
FIG. 25. 3' strategies to diminish the rate of mRNA degradation focuses on 3 putative platforms. The Pseudoknot mediates ribosomal read-through knocking off UPF1 molecules. The RNA stability element acts as a decoy to block UPF1 contact with the 3'UTR avoiding activation of the NMD. Poly(A) tail stem loop structures are used to diminish exosome-mediated mRNA degradation in constructs where a CAP/PABP independent IRES platform is used.

Alternatively, another strategy for extending the life of an mRNA in the cytosol involves interfering with the nonsense-mediated decay pathway. In the canonical pathway, as the ribosome complex hits the gag stop region, the 30 s/50 s subunits disengage from the mRNA, thus rendering the 3' UTR of the mRNA highly susceptible to a UPF-1 mediated decay (FIG. 25, Canonical). Approaches to slow this process have been developed by different viruses including, for example, 3' pseudoknot formation after the gag stop site or introduction of an RNA stability element in the 3'UTR. The 3' pseudoknot mediates a frameshift read-through by the ribosomal complex, thereby knocking UPF-1 complexes off of the 3'UTR, resulting in mRNA stability (FIG. 25, Pseudoknot). The RNA stability element on the other hand, serves as a decoy, directly blocking UPF-1 interaction with the 3'UTR, and thereby stabilizing mRNA against decay (FIG. 25, RNA Stability Element). Poly(A) stem loop structures also can increase mRNA stability by inhibiting exosome-mediated mRNA degradation (FIG. 25, Stem Loop).

Nanoparticles for Delivery of Encapsulated or Unencapsulated mRNAs

Design of efficient gene delivery vectors possessing the high transfection efficiencies and low cytotoxicity is one challenge for delivering modified mRNAs—e.g., $M^2RNA$, $M^3RNA$, or $M^3RNA$-Ig) to cells, tissue, or organs. Nanoparticles represents an exemplary model viral vector-free approach to deliver modified mRNAs. Nanoparticles possess remarkable flexibility for gene delivery including tissue targeting, protect mRNA against nuclease degradation, improve $M^2RNA$ stability through ionic interactions between the negatively charged mRNA and positively charged nanoparticle surface, and increase transformation efficiency for safety. Nanoparticles are generally accepted for therapeutic applications. First, nanoparticles exist in the same size domains as proteins. Second, nanoparticles have large surface areas that can be easily modified using, for example, PEGylation (to increase blood circulation half-life), or a poloxamer, a poloxamine, or chitosan for efficient binding and delivery. Third, modified nanoparticles can have controllable absorption and release properties, particle size, and/or surface characteristics.

A wide variety of organic (lipid-based), inorganic, or hybrid materials are used to produce nanoparticles and are discussed in detail above. In some embodiments, cationic polymer nanoparticles are used to microencapsulate modified messenger RNA. Cationic polymers have positively charged groups in their backbone to interact with negatively charged mRNA-Ig molecules to form neutralized, nanometer-sized complexes.

Multiple metallic nanoparticles have been suggested to cause minimum cytotoxicity. In various embodiments, nanoparticles made of iron, silver, gold, or copper can be used, alone or in combination with other nanoparticles and/or other delivery technologies, for delivering mRNA-Ig molecules.

Nanoparticles may be surface modified to increase the efficiency of modified RNA molecules, whether $M^2RNA$ (or $M^2RNA$-Ig) or $M^3RNA$ (or $M^3RNA$-Ig). Nanoparticles may be modified to introduce, for example, either a biopolymer or PEGylation to increase blood circulation half-life. In some embodiments for the delivery of $M^3RNA$-Ig to skeletal muscle, the surface of the nanoparticle may be modified to include a biopolymer. Suitable biopolymers include, for example, collagen, elastin, fibronectin, chitosan, dextran etc. In particular embodiments, the surface of the nanoparticle may be modified with chitosan. Chitosan exhibits a cationic polyelectrolyte nature and therefore provides a strong electrostatic interaction with negatively charged DNA or RNA molecules. Moreover, chitosan carries primary amine groups that makes it a biodegradable, biocompatible, and non-toxic biopolymer that provides protection against DNase or RNase degradation.

In alternative embodiments, the surface of the nanoparticles may be modified by PEGylation. The technique of covalently attaching the polyethylene glycol (PEG) to a given molecule, nanoparticle in this case, is a well-established method in targeted drug delivery systems. PEGylation involves the polymerization of multiple monomethoxy PEG (mPEG) that are represented as $CH_3O-(CH_2-CH_2O)_n-CH_2-CH_2-OH$. Introducing PEG molecules significantly increases the half-life of a nanoparticle due to its increased hydrophobicity, reduces glomerular filtration rate, and/or lowers immunogenicity due to masking of antigenic sites by forming protective hydrophilic shield. Suitable modifications include modifying the surface of the nanoparticles to possess 3000-4000 PEG molecules, which provides a suitable environment for the physical binding of DNA or RNA molecules.

Figure 26:
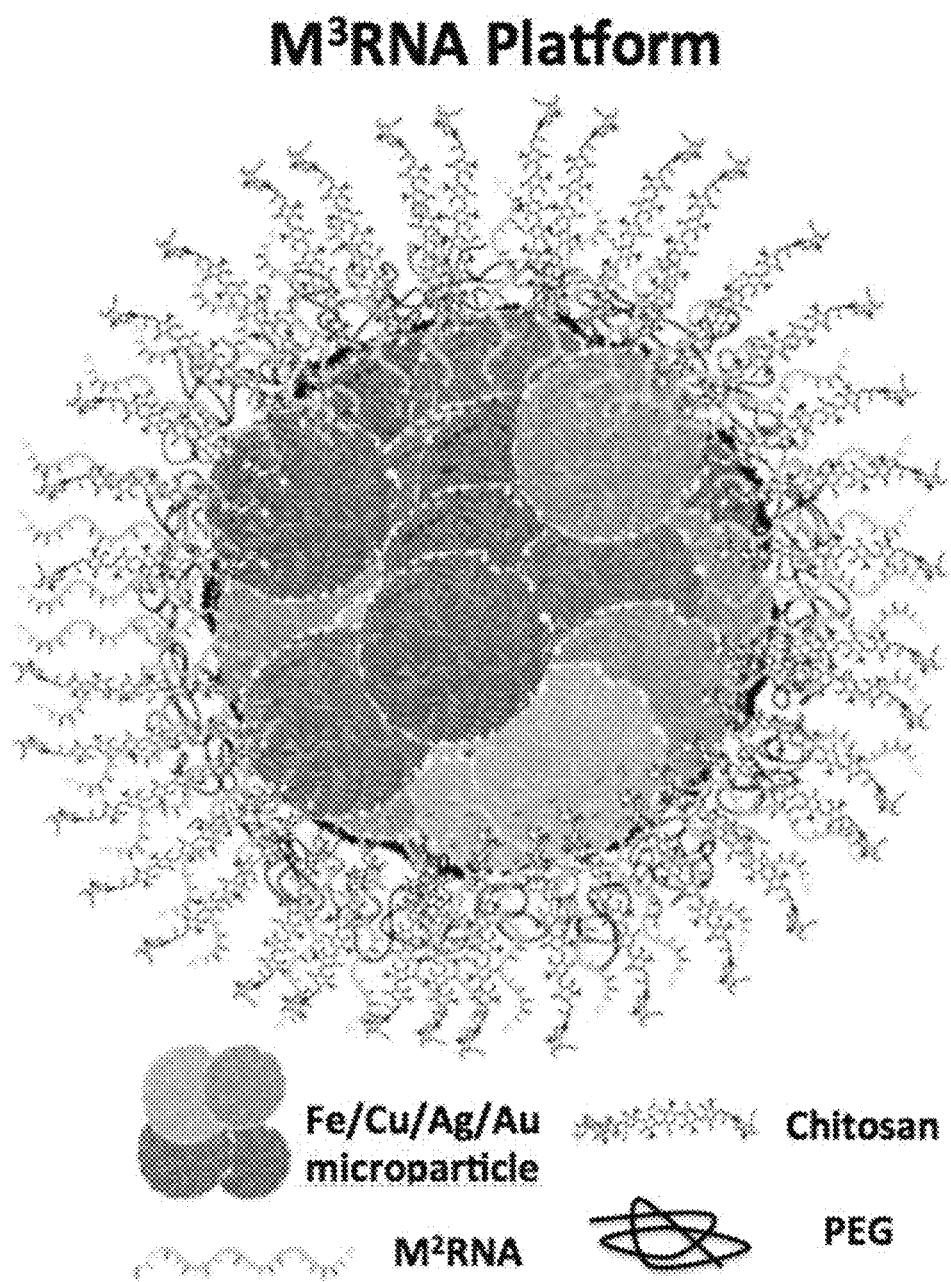
FIG. 26. Combination of M$^2$RNA with microparticles coated with PEG and chitosan yields the putative M$^3$RNA-Ig platform optimized for gene delivery in skeletal muscle.

Taken together, the combination of nanoparticles with PEG, chitosan, and $M^2RNA$ generate the $M^3RNA$ platform (FIG. 26). In the exemplary embodiment illustrated in FIG. 26, the modified mRNA ($M^2RNA$) is encapsulated by the PEG-and-chitosan-coated microparticle since the RNA is indirectly bound to the microparticle through interaction with the chitosan surface modification.

Beyond molecular design, another challenge facing delivery of biologics in muscle tissue is the physical barrier to efficient transfer of biologic payload due, at least in part, to the dense and contractile nature of muscle tissue. Four-dimensional modeling of delivery in tissue using Darcy's Law, a significant limitation has been identified at a level inherent to the design of the needle. By having a straight needle with an end hole, biologics delivery creates a dense pocket of material within skeletal muscle tissue that mimics an abscess. The dense pocket dramatically reduces local tissue uptake of the biologics and preferentially eliminates the biologic via lymphatic and capillary action to alleviate the pressure. Conversely, an adjusted needle design, shown in FIG. 14, devoid of an end hole and utilizing a non-sheering conduit pattern with the delivery needle allows the ability to induce an edema effect instead of an abscess, yielding a much higher degree of tissue accommodation and protracted local exposure of product to tissue. In this way, although the dose of the biologic is not increased the penetrance of the therapy increases by an average of 4-5 fold.

Methods of Using

This document also provides methods of using a particle (e.g., an alginate gel) encapsulating one or more molecules (e.g., biologics) described herein. In some cases, a mammal at risk of experiencing a major adverse cardiac event (e.g., a mammal identified as being likely to experience a major adverse cardiac event as described herein) can be treated by administering a particle encapsulating one or more biologics described herein. For example, a mammal at risk of experiencing a major adverse cardiac event can be treated by administering a particle encapsulating mRNA encoding NAP-2, TGF-α, ErBb3, VEGF, IGF-1, FGF-2, PDGF, IL-2, CD19, CD20, and/or CD80/86 to increase the level of NAP-2, TGF-α, ErBb3, VEGF, IGF-1, FGF-2, PDGF, IL-2, CD19, CD20, and/or CD80/86 polypeptide expression. An increase in the level of one or more of these polypeptides can be used to reduce scar size and tissue remodeling and to improve cardiac function. For example, a mammal at risk of experiencing a major adverse cardiac event can be treated by administering a particle encapsulating an inhibitory RNA targeting eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, and/or MMP-3 to decrease the level of eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, and/or MMP-3 polypeptide expression. A decrease in the level of one or more of these polypeptides can be used to reduce scar size and tissue remodeling and to improve cardiac function.

Any type of mammal experiencing a major adverse cardiac event (e.g., acute myocardial infarction) and/or a mammal at risk of experiencing a major adverse cardiac event (e.g., a mammal who underwent PCI for STEMI) can be treated with using particle-mediated delivery of one or more biologics described herein. For example, humans and other primates such as monkeys experiencing a major adverse cardiac event and/or at risk of experiencing a major adverse cardiac event can be treated with biologics as described herein. In some cases, dogs, cats, horses, cows, pigs, sheep, rabbits, mice, and rats can be treated with biologics as described herein.

Any appropriate method can be used to identify a mammal experiencing a major adverse cardiac event (e.g., acute myocardial infarction) and/or a mammal at risk of experiencing a major adverse cardiac event (e.g., patients who underwent PCI for STEMI). For example, the methods of identifying a mammal at risk of experiencing a major adverse cardiac event described elsewhere (e.g., WO 2015/034897) can be used.

Once identified as experiencing a major adverse cardiac event (e.g., acute myocardial infarction) and/or being at risk of experiencing a major adverse cardiac event, the patient can be administered or instructed to self-administer one or more particles encapsulating a molecule (e.g., a biologic) as described herein.

When treating mammal experiencing a major adverse cardiac event or at risk of experiencing a major adverse cardiac event as described herein, the major adverse cardiac event can be any major adverse cardiac event. Examples of major adverse cardiac events include, without limitation, myocardial infarction (e.g., acute myocardial infarction), heart failure, recurrent myocardial infarction, repeat hospitalization for cardiac-related events, and ischemic heart disease. In some embodiments, the major adverse cardiac event treated as described herein can be myocardial infarction, such as acute myocardial infarction.

In some cases, particle-mediated delivery of one or more molecules (e.g., biologics) to a mammal as described herein can be used to improve cardiac function. Examples of improved cardiac function include, without limitation, increased survivorship, reduced hospitalization, symptom-free tolerance of physical activity, improved global physical fitness, improved cardiac ejection fraction, improved cardiac output, improved stroke volume, improved cardiac mass index, and reduced scar size.

In some cases, particle-mediated delivery of one or more biologics (e.g., mRNA) to a mammal as described herein can be used to increase expression of one or more (e.g., one, two, three, or more) polypeptides useful for regenerating cardiac function and/or tissue. Examples of polypeptides that can be useful for regenerating cardiac function and/or tissue include, without limitation, NAP-2, TGF-α, ErBb3, VEGF, IGF-1, FGF-2, PDGF, IL-2, CD19, CD20, CD80/86, and polypeptides described in WO 2015/034897. An increase in the level of one or more of these polypeptides can be used to reduce scar size and tissue remodeling and/or improve cardiac function. Methods for increasing expression of a polypeptide useful for regenerating cardiac function and/or tissue in cells (e.g., cardiomyocytes) can include contacting the cells with one or more particles encapsulating, for example, an mRNA encoding the polypeptide. One or more particles encapsulating an mRNA encoding the polypeptide can be contacted with the cells by any appropriate method. The term "increased expression" as used herein with respect to the level of a polypeptide is any level that is greater than (e.g., at least about 10, 15, 20, or 25 percent greater than) a reference level for that polypeptide. The term "reference level" as used herein with respect to a polypeptide is the level of expression of that polypeptide typically observed by healthy humans or humans with a low risk of experiencing a major adverse cardiac event. For example, levels of NAP-2, TGF-α, and ErBb3 expression with respect to healthy humans or humans with a low risk of experiencing a major adverse cardiac event can be as described elsewhere (e.g., WO 2015/034897). In some cases, particle-mediated delivery of one or more biologics (e.g., mRNA) to a mammal as described herein can be used to increase expression of NAP-2 and/or TGF-α.

In some cases, particle-mediated delivery of one or more biologics (e.g., inhibitory RNA) to a mammal described herein can be used to decrease expression of one or more (e.g., one, two, three, four, five, six, seven, eight, nine, ten, or more) of the following polypeptides: eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, MMP-3, and polypeptides described in WO 2015/034897. A decrease in the expression level of one or more of these polypeptides can be used to reduce scar size and tissue remodeling and/or improve cardiac function. Methods for decreasing expression of one or more of eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, and MMP-3 in cells can include contacting the cells (e.g., cardiomyocytes) with one or more particles encapsulating, for example, an inhibitory RNA. One or more particles encapsulating an inhibitory RNA can be contacted with the cells by any appropriate method. For example, in humans, a particle encapsulating an inhibitory RNA described herein can be used to decrease expression of a human eotaxin-3, a human cathepsin-S, a human DK-1, a human follistatin, a human ST-2, a human GRO-α, a human IL-21, a human NOV, a human transferrin, a human TIMP-2, a human TNFαRI, a human TNFαRII, a human angiostatin, a human CCL25, a human ANGPTL4, a human MMP-3, or any combination thereof. The term "decreased expression" as used herein with respect to the level of a polypeptide (e.g., eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, or MMP-3) is any level that is lower than (e.g., at least about 10 percent, at least about 15 percent, at least about 20 percent, or at least about 25 percent lower than) a reference level for that polypeptide. The term "reference level" as used herein with respect to a eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, or MMP-3 polypeptide is the level of expression of that polypeptide typically observed by healthy humans or humans with a low risk of experiencing a major adverse cardiac event. Levels of eotaxin-3, cathepsin-S, DK-1, follistatin, ST-2, GRO-α, IL-21, NOV, transferrin, TIMP-2, TNFαRI, TNFαRII, angiostatin, CCL25, ANGPTL4, and MMP-3 expression with respect to healthy humans or humans with a low risk of experiencing a major adverse cardiac event can be as described elsewhere (e.g., WO 2015/034897).

A particle (e.g., an alginate gel) encapsulating one or more molecules (e.g., biologics) described herein can be administered to a mammal experiencing a major adverse cardiac event or likely to experience a major adverse cardiac event as a combination therapy with one or more additional agents/therapies used to treat a major adverse cardiac event. For example, a combination therapy used to treat a mammal identified as being likely to experience a major adverse cardiac event as described herein can include administering an alginate gel encapsulating one or more biologics described herein and treating with aggressive pharmacotherapy (e.g., beta-adrenoceptor blockade, angiotensin converting enzyme inhibitors, aldosterone antagonism treatments, and/or antiplatelet agents), hemodynamic support (e.g., intra-aortic balloon pump and/or mechanical augmentation of cardiac output), surgical intervention (e.g., coronary bypass grafting or left ventricular assist device placement), and/or device-based intervention (e.g., resynchronization therapy or implantable cardiac defibrillators).

In embodiments where a particle (e.g., an alginate gel) encapsulating one or more molecules (e.g., biologics) described herein is used in combination with additional agents/therapies used to treat a major adverse cardiac event, the one or more additional agents can be administered at the same time or independently. For example, an alginate gel encapsulating one or more biologics described herein can be administered first, and the one or more additional agents administered second, or vice versa. In embodiments where a particle (e.g., an alginate gel) encapsulating one or more biologics described herein is used in combination with one or more additional therapies used to treat a major adverse cardiac event, the one or more additional therapies can be performed at the same time or independently of the administration of one or more particles encapsulating one or more biologics described herein. For example, the one or more alginate gels encapsulating one or more biologics described herein can be administered before, during, or after the one or more additional therapies are performed.

In some cases, a particle (e.g., an alginate gel) encapsulating one or more molecules (e.g., biologics) described herein can be used to treat numerous other diseases and/or conditions including, without limitation, a hematologic disorder or hematologic malignancy (e.g., lymphoma, lymphocytic leukemia, myeloma, myelogenous leukemia (e.g., acute myelogenous leukemia and chronic myelogenous leukemia), myelodysplastic syndromes, and myeloproliferative diseases), a musculoskeletal disorder (e.g., carpal tunnel syndrome, epidondylitis, tendinitis, back pain, tension neck syndrome, and hand-arm vibration syndrome), a pulmonary condition (e.g., asthma, chronic obstructive pulmonary disease, chronic bronchitis, emphysema, acute bronchitis, cystic fibrosis, pneumonia, tuberculosis, emphysema, pulmonary edema, acute respiratory distress syndrome, pneumoconiosis, and interstitial lung disease), a gastrointestinal, colorectal, anal-sphincter and/or pelvic organ disease (e.g., enterocolitis, infectious diarrhea, mesenteric ischaemia, inflammatory bowel disease, and pelvic inflammatory disease), a neurologic, spinal cord and/or intracranial disease (e.g., neural tube defects, cephalic disorders, raised or decreased intracranial pressure, meningitis, neuropathies, motor neuron diseases, demyelinating neuropathies, and nerve injuries), a dermatologic disorder (e.g., eczema (e.g., atopic dermatitis), warts, acne, and roseola), chronic inflammatory conditions (e.g., asthma, chronic peptic ulcer, tuberculosis, rheumatoid arthritis, chronic periodontitis, ulcerative colitis and crohn's disease, chronic sinusitis, chronic active hepatitis), and/or genetic defects.

In some cases, a particle (e.g., an alginate gel) encapsulating one or more molecules (e.g., biologics) described herein can be formulated into a pharmaceutically acceptable composition for administration to a mammal experiencing a major cardiac event or at risk of experiencing a major cardiac event. For example, a therapeutically effective amount of an alginate gel encapsulating a biologic described herein can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing a particle (e.g., an alginate gel) encapsulating one or more molecules (e.g., biologics) described herein can be designed for oral, parenteral (including subcutaneous, intraarterial, intramuscular, intravenous, intracoronary, intradermal, or topical), or inhaled administration. When being administered orally, a pharmaceutical composition containing a particle (e.g., an alginate gel) encapsulating one or more biologics described herein can be in the form of a pill, tablet, or capsule.

Compositions suitable for parenteral administration include aqueous and non-aqueous sterile injection solutions that can contain anti-oxidants, buffers, bacteriostats, and solutes which render the formulation isotonic with the blood of the intended recipient; and aqueous and non-aqueous sterile suspensions which may include suspending agents and thickening agents. Compositions for inhalation can be delivered using, for example, an inhaler, a nebulizer, and/or a dry powder inhaler. The formulations can be presented in unit-dose or multi-dose containers, for example, sealed ampules and vials, and may be stored in a freeze dried (lyophilized) condition requiring only the addition of the sterile liquid carrier, for example water for injections, immediately prior to use. Extemporaneous injection solutions and suspensions may be prepared from sterile powders, granules, and tablets.

A pharmaceutically acceptable composition including a particle (e.g., an alginate gel) encapsulating one or more molecules (e.g., biologics) described herein can be administered locally or systemically. In some cases, a composition containing a particle encapsulating one or more biologics described herein can be administered systemically by venous or oral administration to, or inhalation by a mammal (e.g., a human). In some cases, a composition containing a particle encapsulating one or more biologics described herein can be administered locally by percutaneous, subcutaneous, intramuscular, or open surgical administration (e.g., injection) to a target tissue (e.g., cardiac infarct bed) of a mammal (e.g., a human), or by arterial administration to the vascular supply of a target tissue (e.g., cardiac infarct bed) of a mammal (e.g., a human). For example, arterial administration of an alginate gel encapsulating one or more biologics described herein to the vascular supply of the heart can be used to deliver the biologics to the cardiac infarct bed of a human.

Effective doses can vary depending on the severity of the major cardiac event, the route of administration, the age and general health condition of the subject, excipient usage, the possibility of co-usage with other therapeutic treatments such as use of other agents, and the judgment of the treating physician.

The frequency of administration can be any frequency that improves cardiac function without producing significant toxicity to the mammal. For example, the frequency of administration can be from about once a week to about three times a day, from about twice a month to about six times a day, or from about twice a week to about once a day. The frequency of administration can remain constant or can be variable during the duration of treatment. A course of treatment with a composition containing a particle (e.g., an alginate gel) encapsulating one or more biologics described herein can include rest periods. For example, a composition containing an alginate gel encapsulating one or more biologics described herein can be administered daily over a two-week period followed by a two week rest period, and such a regimen can be repeated multiple times. As with the effective amount, various factors can influence the actual frequency of administration used for a particular application. For example, the effective amount, duration of treatment, use of multiple treatment agents, route of administration, and severity of the major cardiac event may require an increase or decrease in administration frequency.

An effective duration for administering a composition containing a particle (e.g., an alginate gel) encapsulating one or more molecules (e.g., biologics) described herein can be any duration that improves cardiac function without producing significant toxicity to the mammal. For example, the effective duration can vary from several days to several weeks, months, or years. In some cases, the effective duration for the treatment of a major cardiac event can range in duration from about one month to about 10 years. Multiple factors can influence the actual effective duration used for a particular treatment. For example, an effective duration can vary with the frequency of administration, effective amount, use of multiple treatment agents, route of administration, and severity of the major cardiac event being treated.

In certain instances, a course of treatment and the cardiac function of the mammal being treated for a major cardiac event can be monitored. Any appropriate method can be used to monitor cardiac function. For example, cardiac function can be assessed using blood tests, electrocardiography (ECG/EKG), cardiac stress testing, coronary catheterization, echocardiogram, and/or intravascular ultrasound at different time points.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Figure 3:
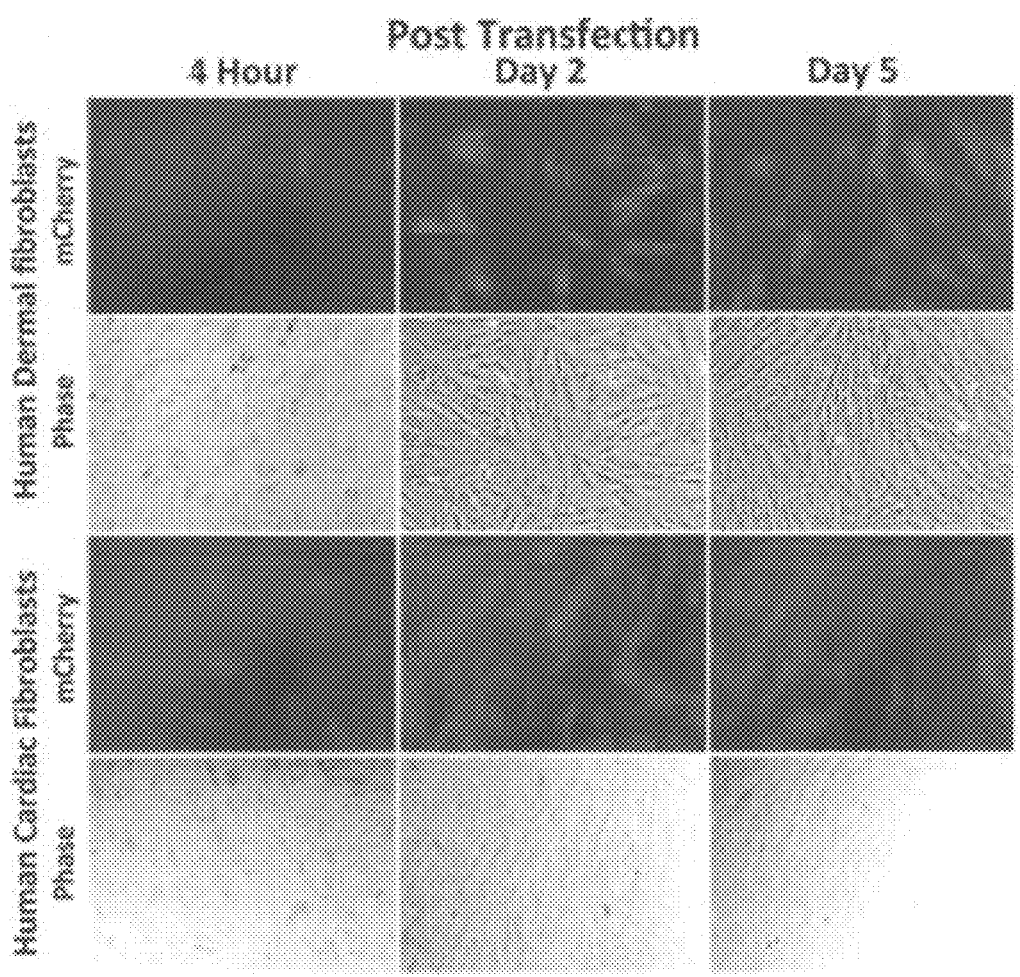
FIG. 3. Fluorescent (first and third rows) and light phase (second and fourth rows) microscopy images showing mCherry transfection in human dermal fibroblasts (top two rows) and human cardiac fibroblasts (bottom two rows).

Example 1: mRNA Expression in Fibroblasts mCherry mRNA was transfected into human dermal fibroblasts and human cardiac fibroblasts. Light phase and fluorescent microscopy was used to evaluate mRNA expression at 4 hours, 2 days, and 5 days post transfection (FIG. 3).

These results demonstrated that mRNA can be sustainably expressed in dermal and cardiac fibroblasts.

Figure 4:
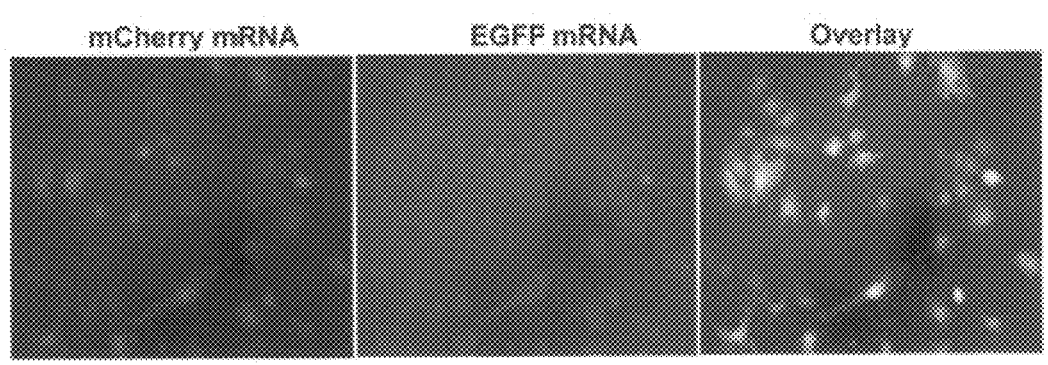
FIG. 4. Fluorescent microscopy images showing co-transfection of EGFP and mCherry in BEK 293 cells.

Example 2: mRNA Co-Expression in Epithelial Cells mCherry mRNA and EGFP mRNA were transfected into HEK293 cells. Multi-channel fluorescent microscopy was used to evaluate mRNA expression at 24 hours post transfection (FIG. 4).

These results demonstrated that multiple mRNAs can be co-expressed.

Figure 5:
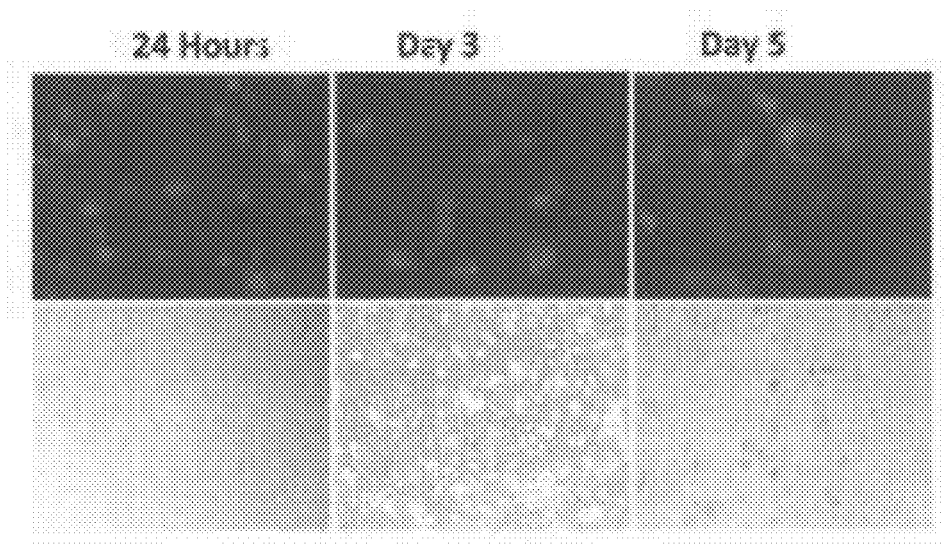
FIG. 5. Fluorescent (top row) and light phase (bottom row) microscopy images showing transfection of mCherry in HL-1 cardiomyocytes.

Example 3: mRNA Expression in Cardiomyocytes mCherry mRNA was transfected into HEK293 cells. Light phase and fluorescent microscopy was used to evaluate mRNA expression at 24 hours, 3 days, and 5 days post transfection (FIG. 5).

These results demonstrated that mRNA can be sustainably expressed in cardiomyocytes.

Example 4: In Vivo Expression of Subcutaneous Liposome-Delivered mRNA

Figure 6:
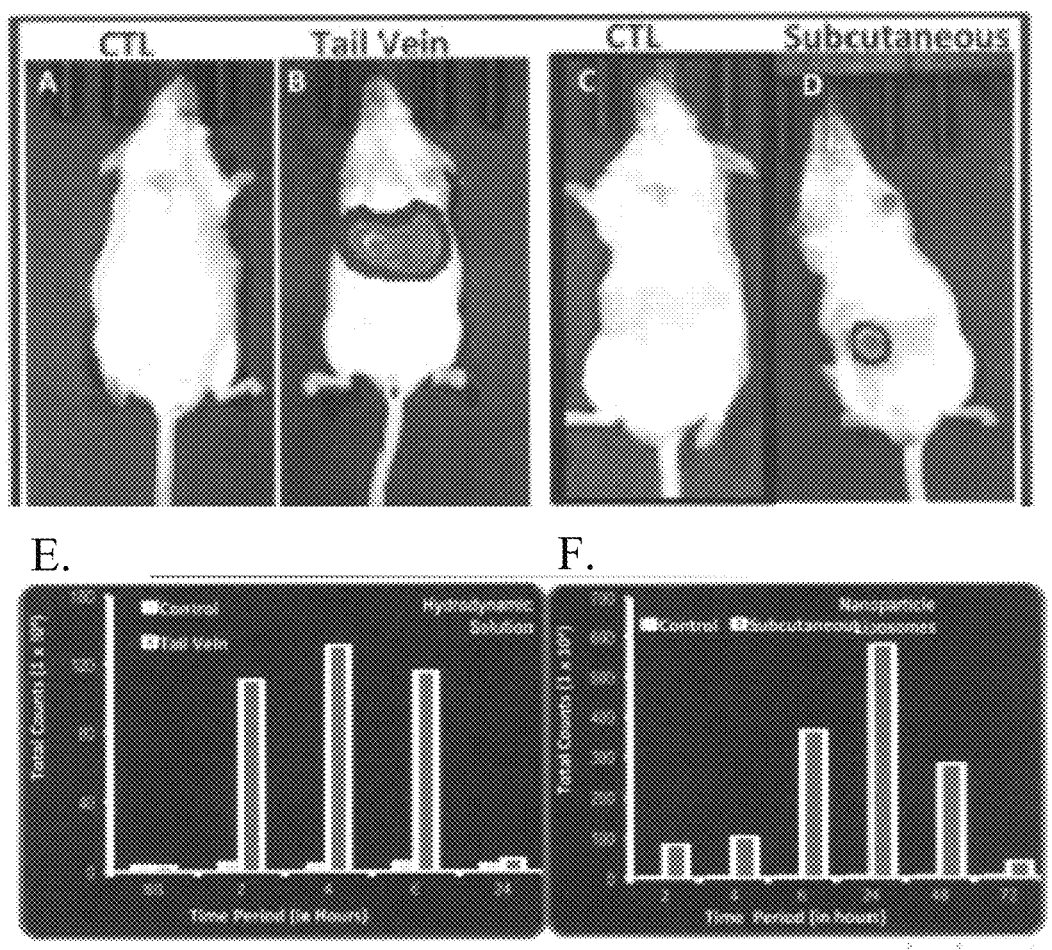
FIG. 6. Data showing particle-mediated delivery of mRNA in a mouse model. (A) Tail vein hydrodynamic injection of a control solution (CTL). (B) Tail vein hydrodynamic injection of liposomes containing luciferase mRNA. (C) Subcutaneous injection of a control solution (CTL). (D) Subcutaneous injection of luciferase mRNA. (E) A bar graph showing the amount of luciferase expressed by the mice in (A) and (B). (F) A bar graph showing the amount of luciferase expressed by the mice in (C) and (D).

Mice were administered a solution of luciferase mRNA via hydrodynamic tail vein injection (FIGS. 6(A) and (B)) or administered liposomes containing luciferase mRNA via subcutaneous injection (FIGS. 6(C) and (D)). Luciferase expression was imaged using a Xenogen (IVIS) imaging system. For mice administered a solution of luciferase mRNA via hydrodynamic tail vein injection, the amount of luciferase expressed was evaluated at the beginning of the experiment and at two hours, four hours, six hours, and 24 hours after administration (FIG. 6E). For mice administered liposomes containing luciferase mRNA via subcutaneous injection, the amount of luciferase expressed was evaluated at two hours, four hours, six hours, 24 hours, 48 hours, and 72 hours after administration (FIG. 6F).

Figure 7:
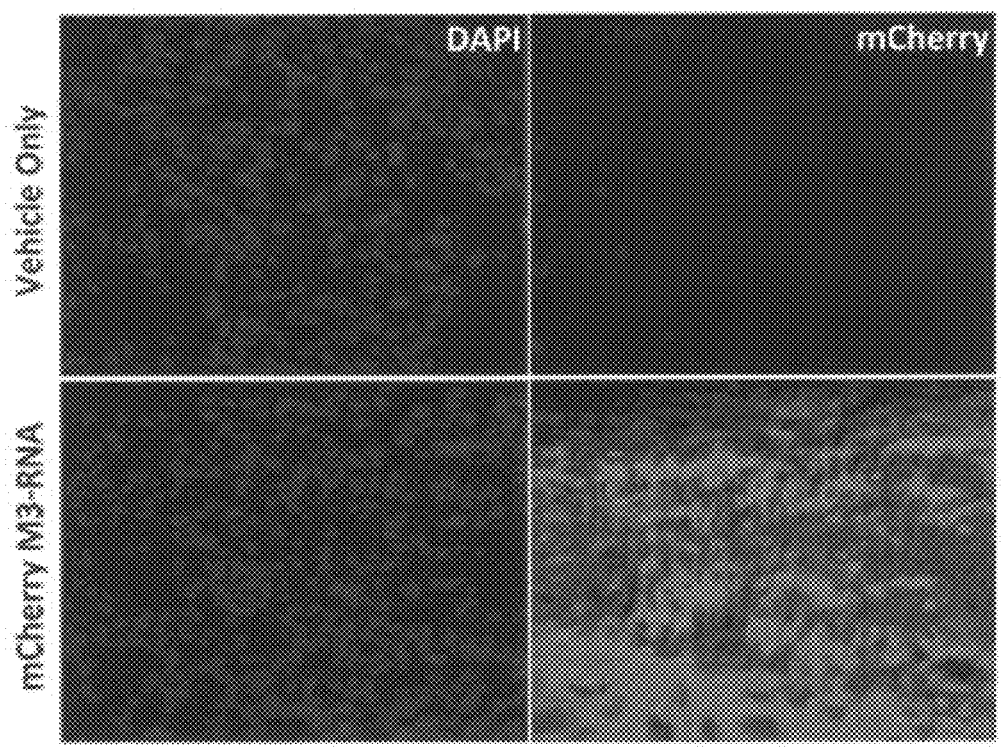
FIG. 7. Microscopy images showing mCherry expression in mice subjected to subcutaneous injection of a control solution (vehicle only; top row) or liposomes containing mCherry RNA (bottom row).

Mice were administered liposomes containing mCherry mRNA via subcutaneous injection. mCherry expression was evaluated using fluorescent microscopy (FIG. 7).

These results demonstrated that liposome delivered mRNA can be sustainably expressed in vivo following subcutaneous administration.

Example 5: In Vivo Expression of Intracardiac Liposome-Delivered mRNA

Figure 8:
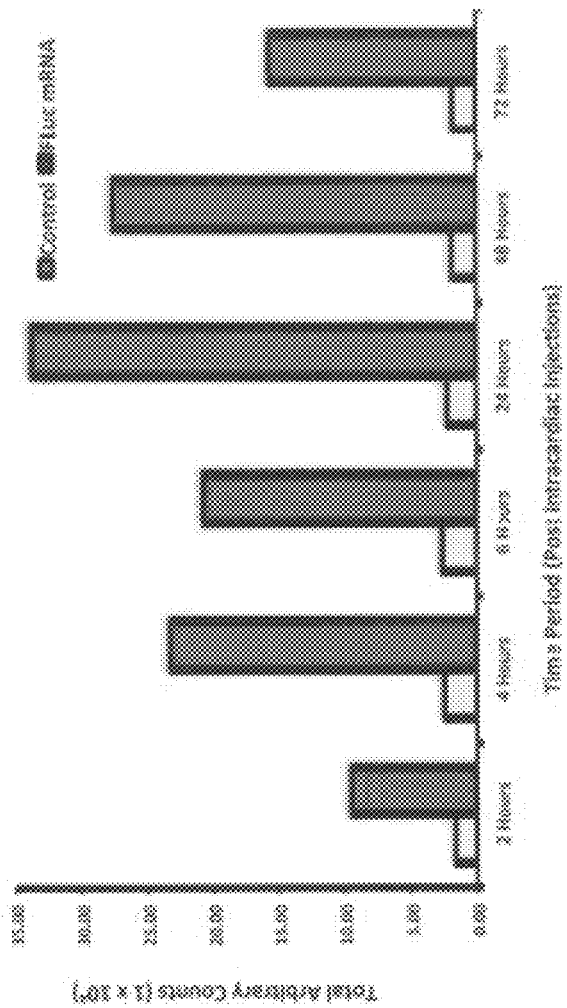
FIG. 8. Data showing particle-mediated delivery of mRNA in a mouse model. (A) A photograph of mice injected with a control solution or liposomes containing luciferase mRNA by echo guided intracardiac injection. (B) A bar graph showing the amount of luciferase expressed by the mice in (A).
Figure 8:
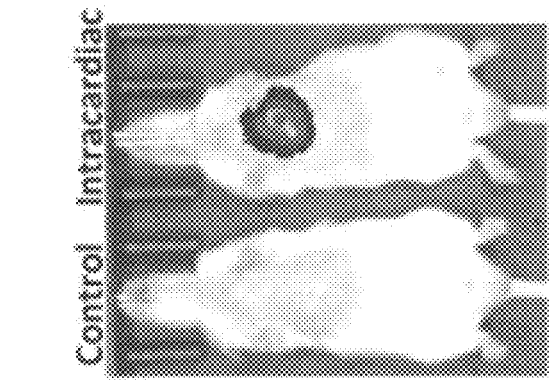

Mice were administered liposomes containing luciferase mRNA via echo guided intracardiac injection (FIG. 8A). Luciferase expression was imaged using a Xenogen (IVIS) imaging system. The amount of luciferase expressed was evaluated at 2, 4, 6, 24, 48, and 72 hours after administration (FIG. 8B).

These results demonstrated that liposome delivered mRNA can be sustainably expressed in vivo following intracardiac administration.

Figure 9:
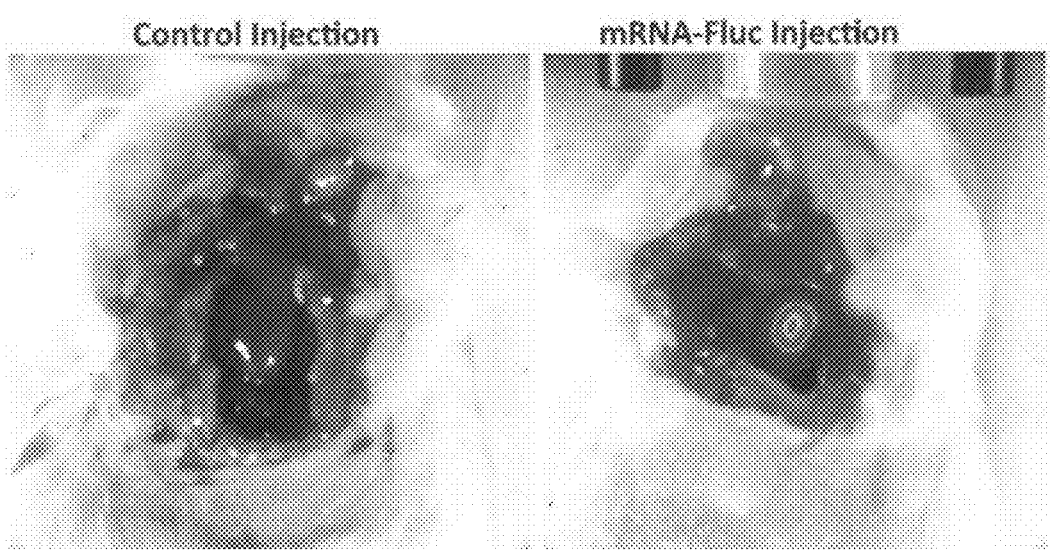
FIG. 9. Photographs of mouse hearts injected with a control solution or liposomes containing luciferase mRNA by open chest intracardiac injection.

Example 6: In Vivo Expression of Open-Chest Intracardiac Liposome-Delivered mRNA Mice were administered liposomes containing luciferase mRNA via open chest intracardiac injection. Luciferase expression was imaged using a Xenogen (IVIS) imaging system (FIG. 9).

These results demonstrated that liposome delivered mRNA can be sustainably expressed in vivo following intracardiac administration.

Example 7: In Vivo Expression of Alginate-Delivered mRNA

Figure 10:
FIG. 10. A photograph of a cross-section of a porcine heart injected with an alginate gel in-Cherry reporter system.

Pigs were administered alginate gel containing mCherry mRNA using previous reported approaches. The amount of mCherry expression was evaluated after the administration (FIG. 10).

Previous methods of using alginate delivery of mRNA resulted in sequestration of biologics within the polymerized product with no intramyocardial expression.

Example 8: In Vivo Expression of Alginate-Delivered mRNA

Pigs were administered a reduced volume of alginate gel containing mCherry mRNA. mCherry expression was evaluated using fluorescent microscopy.

Figure 11:
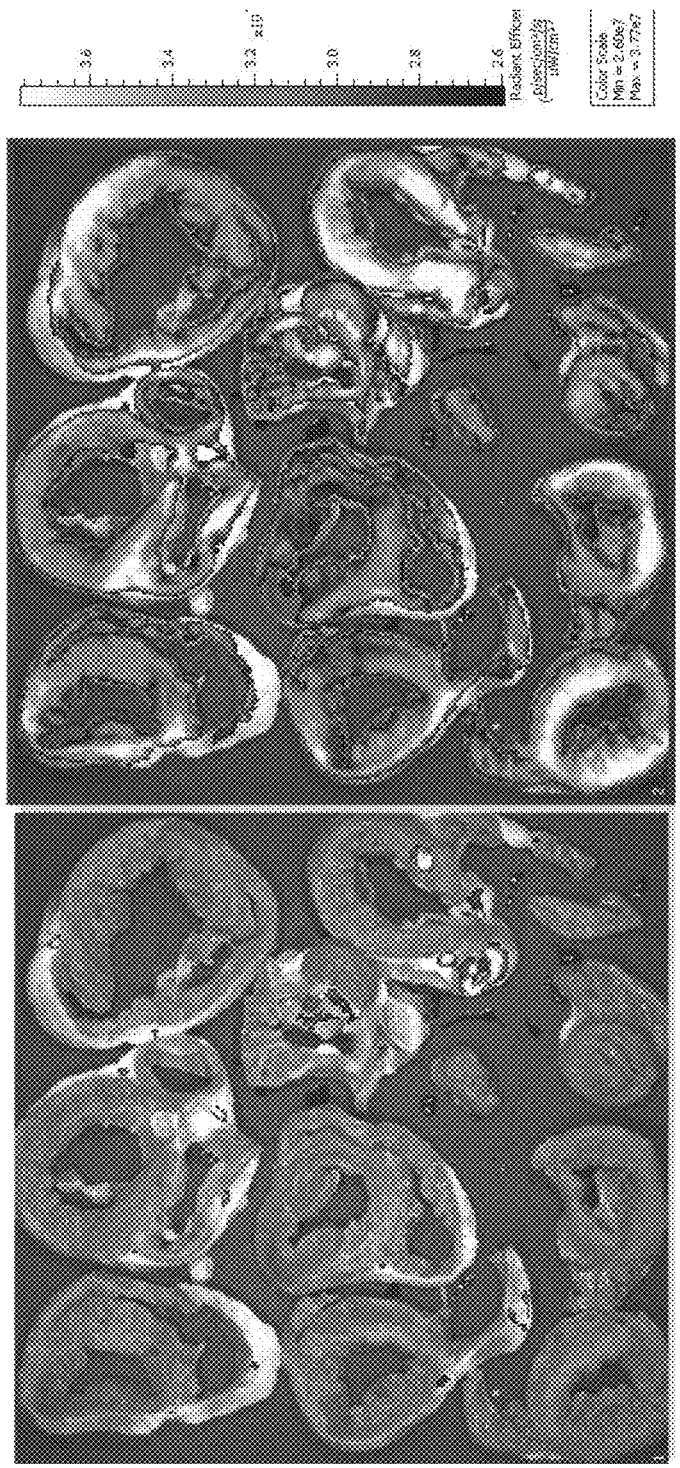
FIG. 11. Fluorescent images of porcine hearts injected with a reduced alginate gel volume.

Reduced alginate gel volume resulted in diffuse delivery of biologics and loss of the majority of signal (3.6 radiance efficiency; FIG. 11).

Example 9: In Vivo Expression of Alginate-Delivered mRNA

Pigs were administered alginate gels having varied alginate/calcium concentrations containing mCherry mRNA. mCherry expression was evaluated using fluorescent microscopy.

Figure 12:
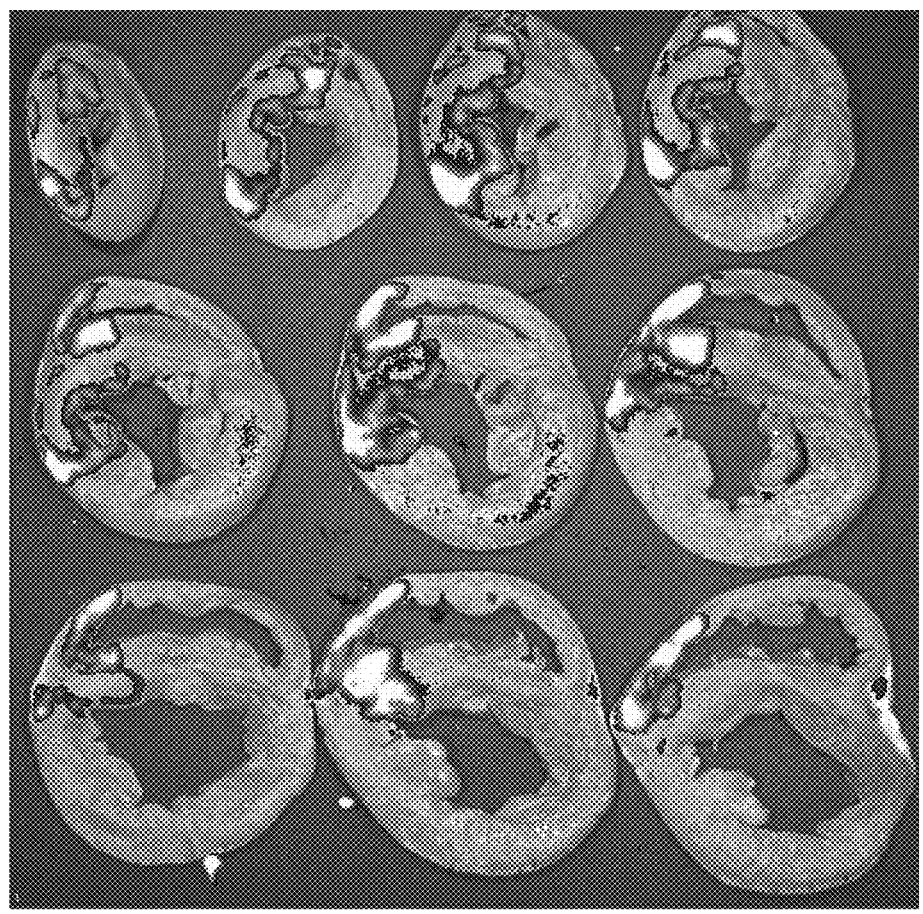
FIG. 12. Fluorescent images of porcine hearts injected with varied alginate/calcium concentrations.

Targeted delivery into the infarct bed with an alginate/calcium gel remaining liquid in blood and escaping into the infarcted capillary bed where it polymerized and delivered the biologics with high efficiency (localized radiance level >10 versus 3-4 in prior efforts; FIG. 12).

These results demonstrated that alginate gel delivered mRNA can be targeted to infarcted capillary beds.

Example 10: In Vivo Expression of Open-Chest Intracardiac Alginate-Delivered mRNA Mice were administered alginate gels having varied alginate/calcium concentrations containing mCherry mRNA. mCherry expression was evaluated using fluorescent microscopy.

Figure 13:
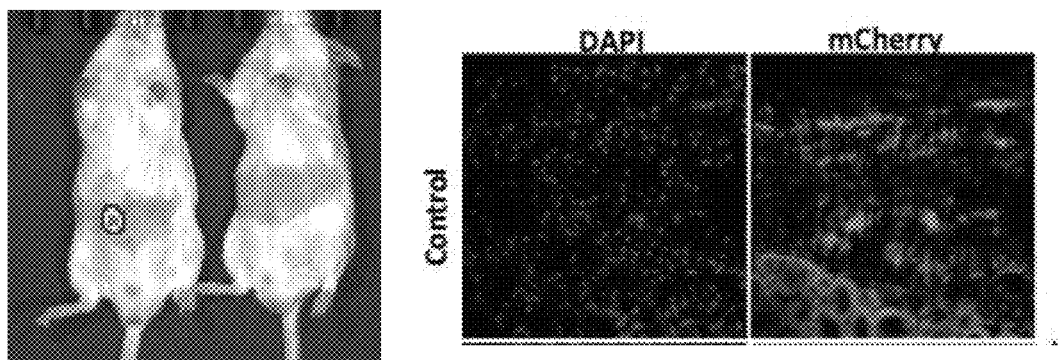
FIG. 13. Fluorescent images following administration of alginate spheres containing mCherry mRNA.

Alginate gel delivery resulted in sustained release of mCherry mRNA (FIG. 13).

These results demonstrated that alginate gel delivered mRNA can be sustainably expressed in vivo following delivery.

```
Sequence Listing Free Text
                                         SEQ ID NO: 1
CCCATTGTAT GGGATCTGAT CTGGGGCCTC GGTGCACATG

CTTTACATGT GTTTAGTCGA GGTTAAAAAA

SEQ ID NO: 2
ACGTCTAGGC CCCCCGAACC ACGGGGACGT GGTTTTCCTTT

GAAAAA
                                         SEQ ID NO: 3
CCAGAAGGTA CCCCATTGTA TGGGATCTGA TCTGGGGCCT

CGGTACACAT GCTTTACATG TGTTTAGTCG AGGTTAAAAA

AACGTCTAGG CCCCCCGAAC CACGGGGACG TGGTTTTCCT

TTGAAAAACA CGATGATA

SEQ ID NO: 4
ATATGGCCAC AACCATGGTG AGCAAGGGCG AGGAGCTGTT

CACCGGGGTG GTGCCCATCC TGGTCGAGCT GGACGGCGAC

GTAAACGGCC ACAAGTTCAG CGTGTCCGGC GAGGGCGAGG

GCGATGCCAC CTACGGCAAG CTGACCCTGA AGTTCATCTG

CACCACCGGC AAG

SEQ ID NO: 5
GCTGCTGCCC GACAACCACT ACCTGXAGCX ACCCAGTCCG

CCCTGAGCAA AGACCCCAAC GAGAAGCGCG ATCACATGGT

CCTGCTGGAG TTCGTGACCG CCGCCGGGAT CACTCTCGGC

ATGGACGAGC TGTACAAGTA AGCCCTGTGG AATGTGTGTC

AGTTAGXXXG GTGTGGAAAG TCCCCAXXGG CTCCCCXXXA

GCAXXXXXXX XXXXXGGCAG AAGTATGCAA AGCATGCATC

TCAATTAGTC AGCAACCAGG TGTGG
```

-continued

SEQ ID NO: 6
CAACGTCTAT ATCATGGCCG ACAAGCAGAA GAACGGCATC
XXXAAGGTGA ACTTCAAGAT CCGCCACAAC ATCGAGGACG
GCAGCGTGCA GCTCGCCGAC CACTACCAGC AGAACACCCC
CATCXGGCGA CGGCCCCGTG CTGCTGCXXC CGACAACCAC

SEQ ID NO: 7
CAACGTCTAT ATCATGGCCG ACAAGCAGAA GAACGGCATC
XXXAAGGTGA ACTTCAAGAT CCGCCACAAC ATCGAGGACG
GCAGCGTGCA GCTCGCCGAC CACTACCAGC AGAACACCCC
CATCXGGCGA CGGCCCCGTG CTGCTGCXXC CGACAACCAC

SEQ ID NO: 8
GCTGAAGCAC TGCACGCCGT AGGTCAGXXG GTGGTCACGA
GGGTGGGCCA GGGCAXCGGG CAGCTTGCCG GTGGTGCAGA
TGAACTTCAG GGTCXXXAGC TTGCCGTAGG TGGCATCGXX
XCCCTCGCCC TCGCCG

SEQ ID NO: 9
GACACGCTGA ACTTGTGGCC GTTTACGTCG CCGTCCAGCT
CGACCAGGAT GGGCXXXACC ACCCCGGTGA ACAGCTCCTC

GCCCTTGCTC ACCXXXATGG TTGTGGCCAT ATTATCATCG
TGTTTTTCAA AGGAAAACCA CGTCCCCGTG GTTCGGGGGG
CCTAGACGTT TTTTTAACCT CGACTAAACA CATXGTAAAG
CATGTGTACC GAGGCCCCAG ATCAGATCCC ATACA

SEQ ID NO: 10
AGGGCACGGG CAGCTTGCCG GTGGTGCAGA TGAACTTCAG
GGTCAGCTTG CCGTAGGTGG CATCGCCCTC GCCCTCGCCX
XXGGACACGC TGAACTTGTG XXXXXXGCCG TTTACGTCGC
CGTCCXXXXX XXXAGCTXXX XXXXXXCGAC CAGGATGGGC
ACCACCCCGG TGAAXXCAGC TCCTCGCCCT TGCTCACCAT
XGGTXXXXXT GTGGCCATAT TATCATCGTG TTTXXXXXXX
XXXTTCAAAG GXXXXAAAAC CACXGTCCCX CGTGGTTCGG
GGGGCCTAGA CGTTTTTTTA ACCTCGACTA AXXXXXCACA
TGTAAAGCAT GTGTACCGAG GCXXXXXXXX XXXCCCAGAT
CAGATCCCAT ACAATGGGGT ACCTTCTGG

---

What is claimed is:

1. A composition comprising a Janus particle encapsulating a biologic compound, the Janus particle comprising:
    a first phase comprising a first exosome, and
    a second phase comprising a second exosome, wherein the first exosome and the second exosome have two or more distinct physical or chemical properties.

2. The composition of claim 1, wherein the biologic compound comprises an mRNA.

3. The composition of claim 1, wherein the biologic compound comprises an inhibitory RNA.

4. The composition of claim 1, wherein the biologic comprises a non-coding RNA.

5. The composition of claim 1, wherein one phase of the Janus particle comprises an alginate gel.

6. The composition of claim 5, wherein the alginate gel comprises a calcium salt.

7. The composition of claim 6, wherein the alginate gel has a ratio of alginate to calcium salt from about 2:1 to about 10:1.

8. The composition of claim 1, wherein the Janus particle has a diameter from about 0.3 μm to about 10 μm in diameter.

9. The composition of claim 1, wherein the Janus particle is polarized or wherein the biphasic particle is charged.

10. The composition of claim 1, wherein the Janus particle comprises a tail.

11. The composition of claim 1, wherein the Janus particle further comprises a scaffold protein.

12. The composition of claim 11, wherein the scaffold protein comprises collagen I, collagen II, collagen III, collagen IV, fibrin, a basement membrane protein, or gelatin.

13. The composition of claim 1, wherein the Janus particle further comprises a scaffold comprising hyaluronic acid.

14. The composition of claim 1, wherein the Janus particle further encapsulates a polypeptide.

15. The composition of claim 1, wherein the Janus particle further encapsulates a lipopolysaccharide.

* * * * *